(12) United States Patent
Wang et al.

(10) Patent No.: US 10,890,631 B2
(45) Date of Patent: Jan. 12, 2021

(54) ESTIMATING ABSOLUTE PHASE OF RADIO FREQUENCY FIELDS OF TRANSMIT AND RECEIVE COILS IN A MAGNETIC RESONANCE

(71) Applicant: OHIO STATE INNOVATION FOUNDATION, Columbus, OH (US)

(72) Inventors: Jinghua Wang, Mason, OH (US); Yu Ding, Sugar Land, TX (US)

(73) Assignee: Ohio State Innovation Foundation, Columbus, OH (US)

(*) Notice: Subject to any disclaimer, the term of this patent is extended or adjusted under 35 U.S.C. 154(b) by 18 days.

(21) Appl. No.: 16/479,453

(22) PCT Filed: Jan. 19, 2018

(86) PCT No.: PCT/US2018/014365
§ 371 (c)(1),
(2) Date: Jul. 19, 2019

(87) PCT Pub. No.: WO2018/136705
PCT Pub. Date: Jul. 26, 2018

(65) Prior Publication Data
US 2019/0383889 A1    Dec. 19, 2019

Related U.S. Application Data

(60) Provisional application No. 62/448,116, filed on Jan. 19, 2017.

(51) Int. Cl.
*G01R 33/24* (2006.01)
*A61B 5/055* (2006.01)
(Continued)

(52) U.S. Cl.
CPC ............ *G01R 33/246* (2013.01); *A61B 5/055* (2013.01); *G01R 33/36* (2013.01); *G01R 33/5611* (2013.01); *G01R 33/583* (2013.01)

(58) Field of Classification Search
CPC .. G01R 33/246; G01R 33/36; G01R 33/5611; G01R 33/583
See application file for complete search history.

(56) References Cited

U.S. PATENT DOCUMENTS

| 5,001,428 A | 3/1991 | Maier et al. |
| 5,742,163 A * | 4/1998 | Liu .................. G01R 33/56554 324/307 |

(Continued)

FOREIGN PATENT DOCUMENTS

| EP | 2615470 | 7/2013 |
| WO | 2005078470 | 8/2005 |

(Continued)

OTHER PUBLICATIONS

Abdoli, et al., (2016) Phased-array combination for MR spectroscopic imaging using a water reference. Magn Reson Med.. 2016;76(3):733-41.

(Continued)

*Primary Examiner* — Dixomara Vargas
(74) *Attorney, Agent, or Firm* — Meunier Carlin & Curfman LLC

(57) ABSTRACT

Methods and apparatuses for determining spatial distribution of an absolute phase of RF transmit field $B_1^+$ and/or RF receive field $B_1^-$ in an MRI system are described herein. An example method can include selecting a transmit coil for which to measure the absolute phase of the RF transmit field $B_1^+$, exciting nuclear spins in MR nuclei using at least two transmit configurations of the transmit coil, and detecting first and MR signals arising from exciting nuclear spins in MR nuclei using first and second transmit configurations, respectively. The method can also include acquiring first and second sets of complex k-space data from the first and second MR signals, respectively, and estimating an absolute (Continued)

phase $B_1^+$ map of the transmit coil using the first set of complex k-space data and the second set of complex k-space data.

23 Claims, 17 Drawing Sheets

(51) Int. Cl.
  *G01R 33/36* (2006.01)
  *G01R 33/561* (2006.01)
  *G01R 33/58* (2006.01)

(56) References Cited

U.S. PATENT DOCUMENTS

| | | | |
|---|---|---|---|
| 6,268,728 | B1 | 7/2001 | Morrell |
| 6,552,538 | B2 | 4/2003 | Demeester et al. |
| 7,064,546 | B2 | 6/2006 | Feiweier |
| 7,446,526 | B2 | 11/2008 | Cunningham et al. |
| 7,603,158 | B2 | 10/2009 | Nachman et al. |
| 7,768,264 | B1 | 8/2010 | Brau et al. |
| 7,795,870 | B2 | 9/2010 | Sodickson et al. |
| 7,800,368 | B2* | 9/2010 | Vaughan .............. G01R 33/246 324/318 |
| 7,839,147 | B2 | 11/2010 | Katscher et al. |
| 7,859,262 | B2 | 12/2010 | Jellus |
| 8,019,801 | B1* | 9/2011 | Robb .................... G06T 7/0002 707/899 |
| 8,026,720 | B1 | 9/2011 | Chen et al. |
| 8,054,078 | B2 | 11/2011 | Ikezaki |
| 8,076,939 | B2 | 12/2011 | Setsompop et al. |
| 8,077,955 | B2 | 12/2011 | Dannels et al. |
| 8,125,225 | B2 | 2/2012 | Koretsky |
| 8,148,984 | B2 | 4/2012 | Johnson et al. |
| 8,198,891 | B2 | 6/2012 | Sacolick et al. |
| 8,258,786 | B2 | 9/2012 | Hennel |
| 8,305,077 | B2 | 11/2012 | Morrell et al. |
| 8,427,156 | B2 | 4/2013 | Kholmovski et al. |
| 8,446,149 | B2 | 5/2013 | Heberlein et al. |
| 8,502,534 | B2 | 8/2013 | Lai et al. |
| 8,502,538 | B2 | 8/2013 | Dannels et al. |
| 8,558,547 | B2 | 10/2013 | Sacolick et al. |
| 8,736,265 | B2 | 5/2014 | Boernert et al. |
| 8,805,042 | B2 | 8/2014 | Weiss |
| 8,831,318 | B2 | 9/2014 | Sharif et al. |
| 8,891,846 | B2 | 11/2014 | Fautz |
| 8,994,372 | B2 | 3/2015 | Bitz et al. |
| 9,018,951 | B2 | 4/2015 | Lai et al. |
| 9,035,653 | B2 | 5/2015 | Hutter et al. |
| 9,069,998 | B2 | 6/2015 | Bulumulla et al. |
| 9,086,446 | B2 | 7/2015 | Schulte et al. |
| 9,229,074 | B2 | 1/2016 | Voigt et al. |
| 9,274,197 | B2 | 3/2016 | Wang et al. |
| 9,279,873 | B2 | 3/2016 | Xue et al. |
| 9,297,873 | B2 | 3/2016 | Block et al. |
| 9,307,925 | B2 | 4/2016 | Russell et al. |
| 9,389,293 | B2 | 7/2016 | Stemmer |
| 9,417,305 | B2 | 8/2016 | Zhai et al. |
| 9,478,051 | B2 | 10/2016 | Li et al. |
| 9,684,050 | B2* | 6/2017 | Purdy ................... G01R 33/565 |
| 9,709,653 | B2* | 7/2017 | Wheaton ............... G01R 33/24 |
| 9,903,921 | B2* | 2/2018 | Sodickson ............. A61B 5/055 |
| RE47,026 | E* | 9/2018 | Vaughan ............ G01R 33/5612 |
| 10,145,929 | B2* | 12/2018 | Stemmer ............. G01R 33/543 |
| 10,317,489 | B2* | 6/2019 | Nickel ............... G01R 33/4828 |
| 2006/0253015 | A1 | 11/2006 | Nezafat et al. |
| 2008/0024132 | A1 | 1/2008 | Brau et al. |
| 2008/0129298 | A1* | 6/2008 | Vaughan ............ G01R 33/5659 324/322 |
| 2009/0238449 | A1* | 9/2009 | Zhang ..................... G06T 7/521 382/165 |
| 2010/0239151 | A1 | 9/2010 | Dannels et al. |
| 2010/0253336 | A1 | 10/2010 | Schneider et al. |
| 2010/0260397 | A1* | 10/2010 | Block ................ G01R 33/5614 382/131 |
| 2010/0286500 | A1 | 11/2010 | Ruhm |
| 2011/0025327 | A1 | 2/2011 | Deoni et al. |
| 2011/0026799 | A1 | 2/2011 | Nehrke et al. |
| 2012/0002858 | A1 | 1/2012 | Huang et al. |
| 2012/0007600 | A1 | 1/2012 | Boernert et al. |
| 2012/0150458 | A1 | 6/2012 | Sodickson et al. |
| 2012/0280683 | A1 | 11/2012 | Sacolick et al. |
| 2012/0306493 | A1 | 12/2012 | Voigt et al. |
| 2012/0306499 | A1 | 12/2012 | Hamamura et al. |
| 2013/0134972 | A1 | 5/2013 | Schulte et al. |
| 2013/0251227 | A1 | 9/2013 | Wang et al. |
| 2014/0056496 | A1 | 2/2014 | Kwak et al. |
| 2014/0103925 | A1 | 4/2014 | Hancu et al. |
| 2014/0152308 | A1 | 6/2014 | Lee et al. |
| 2014/0232393 | A1* | 8/2014 | Wheaton ................ G01R 33/24 324/309 |
| 2014/0300354 | A1 | 10/2014 | He et al. |
| 2014/0340083 | A1 | 11/2014 | Zhang et al. |
| 2015/0310641 | A1* | 10/2015 | Purdy .................. G01R 33/565 382/131 |
| 2015/0355306 | A1* | 12/2015 | Stemmer .......... G01R 33/56563 324/309 |
| 2016/0054262 | A1 | 2/2016 | Sodickson et al. |
| 2016/0061921 | A1 | 3/2016 | Katscher et al. |
| 2016/0169995 | A1* | 6/2016 | Nickel ............... G01R 33/4828 324/309 |

FOREIGN PATENT DOCUMENTS

| | | |
|---|---|---|
| WO | 2009118688 | 10/2009 |
| WO | 2009118702 | 10/2009 |
| WO | 2010032172 | 3/2010 |
| WO | 2012054329 | 4/2012 |
| WO | 2012140536 | 10/2012 |
| WO | 2015158625 | 10/2015 |
| WO | 2016/183572 A1 | 11/2016 |

OTHER PUBLICATIONS

Allen, et al. (2011) Phase-sensitive sodium B1 mapping. Magn Reson Med 65(4):1125-1130.

Ammari, et al., (2015) Magnetic resonance-based reconstruction method of conductivity and permittivity distributions at the Larmor frequency. Inverse Problems. 31(10):105001.

Balezeau, et al., (2011) Mapping of low flip angles in magnetic resonance. Physics in medicine and biology 56(20):6635-6647.

Beatty, et al. Design of k-space channel combination kernels and integration with parallel imaging. Magn Reson Med. 2014;71(6):2139-54.

Benkhedah, et al., Evaluation of adaptive combination of 30-channel head receive coil array data in 23Na MR imaging. Magn Reson Med. 2016;75(2):527-36.

Beqiri, et al., Comparison between simulated decoupling regimes for specific absorption rate prediction in parallel transmit MRI. Magn Reson Med. 2015;74(5):1423-34.

Bhakta, et al., (2008) Principles of electroanatomic mapping. Indian pacing and electrophysiology journal 8(1):32-50.

Blaimer, et al., Comparison of phase-constrained parallel MRI approaches: Analogies and differences. Magnetic Resonance in Medicine. 2016;75(3):1086-99.

Breuer, et al., Dynamic autocalibrated parallel imaging using temporal GRAPPA (TGRAPPA). Magn Reson Med. 2005;53(4):981-5.

Brunner, et al., SVD analysis of Array transmission and reception and its use for bootstrapping calibration. Magnetic resonance in medicine 76.6 (2016): 1730-1740.

Brunner, et al., (2009) B1(+) interferometry for the calibration of RF transmitter arrays. Magn Reson Med 61(6):1480-1488.

Boulant et al., High tip angle approximation based on a modified Bloch-Riccati equation, Magn Reson Med 2012; 67(2):339-43.

By, Samantha, et al. "A 16-channel receive, forced current excitation dual-transmit coil for breast imaging at 7T." PloS one 9.11 (2014): e113969. http://journals.plos.org/plosone/article?id=info:doi/10.1371/journal.pone.0113969.

(56) References Cited

OTHER PUBLICATIONS

Bydder M, Larkman DJ, Hajnal JV. Combination of signals from array coils using image-based estimation of coil sensitivity profiles. Magn Reson Med. 2002;47(3):539-48.

Caeiros, et al., A new image reconstruction algorithm for real-time monitoring of conductivity and permeability changes in Magnetic Induction Tomography. Conference proceedings: Annual International Conference of the IEEE Engineering in Medicine and Biology Society IEEE Engineering in Medicine and Biology Society Conference. 2012; 2012:6239-42.

Chang, (2012) Rapid B1 mapping using orthogonal, equal-amplitude radio-frequency pulses. Magn Reson Med 67(3):718-723.

Chung, et al., (2010) Rapid B1+ mapping using a preconditioning RF pulse with TurboFLASH readout. Magn Reson Med 64(2):439-446.

Cohen, Magnetoencephalography: evidence of magnetic fields produced by alpha-rhythm currents. Science 161.3843 (1968): 784-786.

Collins, Recent and ongoing developments. Electromagnetics in Magnetic Resonance Imaging: Morgan & Claypool Publishers; 2016. p. 6-1-6-.

Cunningham, et al., (2006) Saturated double-angle method for rapid B1+ mapping. Magn Reson Med 55(6):1326-1333.

Dagher, et al., MAGPI: A framework for maximum likelihood MR phase imaging using multiple receive coils. Magnetic Resonance in Medicine. 2016;75(3):1218-31.

Damijan, et al., Electric properties of tissues. Encyclopedia of biomedical engineering, 2006:12 pages.

Degirmenci, et al., Image reconstruction in magnetic resonance conductivity tensor imaging (MRCTI). IEEE Trans Med Imaging. 2012;31(3):525-32.

Doneva, et al., Automatic coil selection for channel reduction in SENSE-based parallel imaging. Magma (New York, NY). 2008;21(3):187-96.

Dowell, et al., (2007) Fast, accurate, and precise mapping of the RF field in vivo using the 180 degrees signal null. Magn Reson Med 58(3):622-630.

Duan, et al., (2013) Improved Bloch-Siegert based B1 mapping by reducing off-resonance shift. NMR Biomed 26(9):1070-1078.

Duyn, et al., High-field MRI of brain cortical substructure based on signal phase. Proceedings of the National Academy of Sciences. 2007;104(28):11796-801.

Duyn, et al., Simple correction method fork-space trajectory deviations in MRI. Journal of Magnetic Resonance. 1998;132(1):150-3.

Eggenschwiler, et al., (2012) SA2RAGE: a new sequence for fast B1+-mapping. Magn Reson Med 67(6):1609-1619.

Feng L, et al. Golden-angle radial sparse parallel MRI: combination of compressed sensing, parallel imaging, and golden-angle radial sampling for fast and flexible dynamic volumetric MRI. Magn Reson Med. 2014;72(3):707-17.

Ferrand, et al., (2014) Accelerating parallel transmit array B1 mapping in high field MRI with slice undersampling and interpolation by kriging. IEEE transactions on medical imaging 33(8):1726-1734.

Gol, et al., A subspace-based coil combination method for phased-array magnetic resonance imaging. Magn Reson Med. 2016;75(2):762-74.

González, et al., Robust phase unwrapping by convex optimization. 2014 IEEE International Conference on Image Processing (ICIP); 2014: IEEE, 6 pages.

Griswold, et al. Generalized autocalibrating partially parallel acquisitions (GRAPPA). Magn Reson Med. 2002;47(6):1202-10.

Hancu, et al., On conductivity, permittivity, apparent diffusion coefficient, and their usefulness as cancer markers at MRI frequencies. Magn Reson Med. 2015;73(5):2025-9.

Hansen, et al., Image reconstruction: An overview for clinicians. Journal of Magnetic Resonance Imaging. 2015;41(3):573-85.

Hoffmann, et al., Numerical and experimental evaluation of RF shimming in the human brain at 9.4 T using a dual-row transmit array. Magnetic Resonance Materials in Physics, Biology and Medicine. 2014;27(5):373-86.

Insko, et al., (1993) Mapping the radiofrequency field. J. Magn. Reson. Ser. A, (103):82-85.

Seo, et al., Electrical tissue property imaging using MRI at dc and Larmor frequency. Inverse Problems. 2012;28, 084002.

Jiru, et al., (2006) Fast 3D radiofrequency field mapping using echo-planar imaging. Magn Reson Med 56(6):1375-1379.

Jordanova, et al., (2014) B1 estimation using adiabatic refocusing: BEAR. Magn Reson Med 72(5):1302-1310.

Kamilov, et al., Isotropic inverse-problem approach for two-dimensional phase unwrapping. JOSA A. 2015;32(6):1092-100.

Kang, et al., (2013) Fast B1 mapping based on interleaved-three-flip-angle (ITFA) excitation. Medical physics 40(11):112301.

Katscher, et al., B(1)-based specific energy absorption rate determination for nonquadrature radiofrequency excitation. Magn Reson Med. 2012: 68:1911-18.

Katscher, et al., Recent progress and future challenges in MR electric properties tomography. Computational and mathematical methods in medicine. 2013;2013:546562.

Katscher, et al., Determination of Electric Conductivity and Local SAR Via B1 Mapping. IEEE transactions on medical imaging. 2009;28(9):1365-74.

Keil, et al., Massively parallel MRI detector arrays. Journal of Magnetic Resonance. 2013;229:75-89.

Khalighi, et al., (2012) RF pulse optimization for Bloch-Siegert B +1 mapping. Magn Reson Med 68(3):857-862.

Kim, et al., LORAKS makes better SENSE: Phase-constrained partial fourier SENSE reconstruction without phase calibration. Magnetic resonance in medicine 77.3 (2017): 1021-1035.

Kimura, et al., Inhomogeneous noise correction combined with uniform filter and sensitivity map (INCUS) for multi-coil imaging including parallel imaging. Magn Reson Med. 2013;12(1):21-30.

Lee S-K, et al., Tissue electrical property mapping from zero echo-time magnetic resonance imaging. IEEE transactions on medical imaging. 2015;34(2):541-50.

Lew, et al., SENSE phase-constrained magnitude reconstruction with iterative phase refinement. Magn Reson Med. 2007;58(5):910-21.

Li, et al., susceptibility mapping of human brain reflects spatial variation in tissue composition. Neuroimage. 2011;55(4):1645-56.

Liu, et al., Inter-echo variance as a weighting factor for multi-channel combination in multi-echo acquisition for local frequency shift mapping. Magn Reson Med. 2015;73(4):1654-61.

Lukzen et al., Analytical derivation of multiple spin echo amplitudes with arbitrary refocusing angle, J Magn Reson 2007, 185(1):71-6.

Lustig, et al., SPIRiT: Iterative self-consistent parallel imaging reconstruction from arbitrary k-space. Magn Reson Med. 2010;64(2):457-71.

Lutti A, et al. (2012) Robust and fast whole brain mapping of the RF transmit field B1 at 7T. PloS one 7(3):e32379.

Lyu, et al., Fast GRAPPA reconstruction with random projection. Magn Reson Med. 2015;74(1):71-80.

Ma, et al., Improved adaptive reconstruction of multichannel MR images. Medical physics. 2015;42(2):637-44.

Marques, et al., Single acquisition electrical property mapping based on relative coil sensitivities: a proof-of-concept demonstration. Magn Reson Med. 2015;74(1):185-95.

Morrell, (2008) A phase-sensitive method of flip angle mapping. Magn Reson Med 60(4):889-894.

Morrell, et al., (2010) An analysis of the accuracy of magnetic resonance flip angle measurement methods. Physics in medicine and biology 55(20):6157-6174.

Murase et al., Numerical solutions to the time-dependent Bloch equations revisited, Magn Reson Imaging 2011; 29(1):126-31.

Nehrke, et al., (2012) DREAM—A novel approach for robust, ultrafast, multislice B(1) mapping. Magn Reson Med 68(5):1517-1526.

Nehrke, et al., (2014) Volumetric B1+ Mapping of the Brain at 7T using DREAM. Magnetic Resonance in Medicine, 71, 246-256.

(56) References Cited

OTHER PUBLICATIONS

Oran, et al., Feasibility of conductivity imaging using subject eddy currents induced by switching of MRI gradients. Magnetic resonance in medicine 77.5 (2017): 1926-1937.
Padormo, et al., Parallel transmission for ultrahigh-field imaging. NMR in Biomedicine. 2016;29(9):1145-61.
Park, et al., (2013) A statistical analysis of the Bloch-Siegert B1 mapping technique. Physics in medicine and biology 58(16):5673-5691.
Parker, et al., Phase reconstruction from multiple coil data using a virtual reference coil. Magn Reson Med. 2014;72(2):563-9.
Peng, et al. Optimized parallel imaging for dynamic PC-MRI with multidirectional velocity encoding. Magn Reson Med. 2010;64(2):472-80.
Perman, (1989) A method for correctly setting the rf flip angle. Magn Reson Med 9(1):16-24.
Rivoire, et al. (2011) Flip-angle measurement by magnetization inversion: Calibration of magnetization nutation angle in hyperpolarized (3) He magnetic resonance imaging lung experiments. Magn Reson Med 65(2):399-408.
Robinson, et al. An illustrated comparison of processing methods for MR phase imaging and QSM: combining array coil signals and phase unwrapping. NMR in Biomedicine 30.4 (2017): e3601.
Robinson, et al. Combining phase images from array coils using a short echo time reference scan (COMPOSER). Magnetic resonance in medicine 77.1 (2017):318-327.
Rodgers, et al., Coil combination for receive array spectroscopy: Are data-driven methods superior to methods using computed field maps? Magn Reson Med. 2016;75(2):473-87.
Roemer, et al., The NMR phased array. Magn Reson Med. 1990;16(2):192-225.
Ropella, et al., A regularized, model-based approach to phase-based conductivity mapping using MRI. Magnetic resonance in medicine 78.5 (2017): 2011-2021.
Sacolick, et a., (2011) Fast radiofrequency flip angle calibration by Bloch-Siegert shift. Magn Reson Med 66(5):1333-1338.
Sacolick, et al., (2010) B1 mapping by Bloch-Siegert shift. Magn Reson Med 63(5):1315-1322.
Saranathan, et al., (2013) Efficient bloch-siegert B1+ mapping using spiral and echo-planar readouts. Magnetic Resonance in Medicine 70(6):1669-1673.
Sbrizzi, et al., RF peak power reduction in CAIPIRINHA excitation by interslice phase optimization. NMR in Biomedicine. 2015;28(11):1393-401.
Sbrizzi, et al., (2014) Robust reconstruction of B 1+ maps by projection into a spherical functions space. Magnetic Resonance in Medicine, 71, 394-401.
Schar, et al., (2010) Simultaneous B(0)- and B(1)+-map acquisition for fast localized shim, frequency, and RF power determination in the heart at 3 T. Magn Reson Med 63(2):419-426.
Schmid, et al., Dielectric properties of human brain tissue measured less than 10 h postmortem at frequencies from 800 to 2450 MHz.Bioelectromagnetics. 2003;24(6):423-30.
Schmidt, et al., A new approach for electrical properties estimation using a global integral equation and improvements using high permittivity materials. Journal of Magnetic Resonance. 2016;262:8-14.
Schulte, et al., (2011) Transmit gain calibration for nonproton MR using the Bloch-Siegert shift. NMR Biomed 24(9):1068-1072.
Sersa I. Enhanced sensitivity current density imaging. J Magn Reson. 2010;204(2):219-24.
Shin, et al. Initial study on in vivo conductivity mapping of breast cancer using MRI. Journal of magnetic resonance imaging 2015;42(2):371-8.
Sigfridsson, et al., In vivo SNR in DENSE MRI; temporal and regional effects of field strength, receiver coil sensitivity and flip angle strategies. Magnetic resonance imaging. 2011;29(2):202-8.
Sotiropoulos, et al., Effects of image reconstruction on fiber orientation mapping from multichannel diffusion MRI: reducing the noise floor using SENSE. Magn Reson Med. 2013;70(6):1682-9.
Stollberger, et al., (1996) Imaging of the active B1 field in vivo. Magn Reson Med 35(2):246-251.
Sung, et al., (2008) B1+ compensation in 3T cardiac imaging using short 2DRF pulses. Magn Reson Med 59(3):441-446.
Sung, et al., (2013) Simultaneous T(1) and B(1) (+) mapping using reference region variable flip angle imaging. Magn Reson Med 70(4):954-961.
Tse, et al., (2014) Encoding methods for B1(+) mapping in parallel transmit systems at ultra-high field. Journal of magnetic resonance (San Diego, Calif.: 997) 245:125-132.
Uecker, et al., ESPIRiT—an eigenvalue approach to autocalibrating parallel MRI: Where SENSE meets GRAPPA. Magn Reson Med. 2014;71(3):990-1001.
Uecker, et al., Estimating absolute-phase maps using ESPIRiT and virtual conjugate coils. Magnetic resonance in medicine77.3 (2017): 1201-1207.
Ueno S. Studies on magnetism and bioelectromagnetics for 45 years: From magnetic analog memory to human brain stimulation and imaging. Bioelectromagnetics. 2012;33(1):3-22.
Van Lier, et al. B 1+ Phase mapping at 7 T and its application for in vivo electrical conductivity mapping. Magn Reson Med. 2012;67(2):552-61.
Van Lier, et al., Electrical properties tomography in the human brain at 1.5, 3, and 7T: a comparison study. Magnetic resonance in medicine 71.1 (2014): 354-363.
Vashaee, et al., (2013) B1 mapping with a pure phase encode approach: quantitative density profiling. Journal of magnetic resonance (San Diego, Calif.: 1997) 232:68-75.
Vegh V, et al., Selective channel combination of MRI signal phase. Magn Reson Med. 2016; 76:1469-1477.
Voigt, et al., Quantitative conductivity and permittivity imaging of the human brain using electric properties tomography. Magn Reson Med. 2011;66(2):456-66.
Wan Y, Negishi M, Constable RT. A feasibility study of magnetic resonance driven electrical impedance tomography using a phantom. Physiological measurement. 2013;34(6):623.
Wang, et al., In vivo method for correcting transmit/receive nonuniformities with phased array coils. Magn Reson Med. 2005;53(3):666-74.
Wang, et al., T1 measurements incorporating flip angle calibration and correction in vivo. J Magn Reson. 2006;182(2):283-92.
Wang, et al., Constable RT. Measurement and correction of transmitter and receiver induced nonuniformities in vivo. Magn Reson Med. 2005;53(2):408-17.
Wang, et al., A new method to derive white matter conductivity from diffusion tensor MRI. IEEE Trans Biomed Eng. 2008;55(10):2481-6.
Wang, et al., (2009) Rapid 3D radiofrequency field mapping using catalyzed double-angle method. NMR Biomed 22(8):882-890.
Weis, et al., (2005) A simple method for mapping the B1 field distribution of linear RF coils. Magma 18(6):283-287.
Yamaguchi-Sekino, et al., Biological effects of electromagnetic fields and recently updated safety guidelines for strong static magnetic fields. Magn Reson Med. 2011;10(1):1-10.
Yarnykh, (2007) Actual flip-angle imaging in the pulsed steady state: a method for rapid three-dimensional mapping of the transmitted radiofrequency field. Magn Reson Med 57(1):192-200.
Zhang, et al., Magnetic-resonance-based electrical properties tomography: a review. IEEE reviews in biomedical engineering. 2014;7:87-96.
Zhang, et al., Complex B1 mapping and electrical properties imaging of the human brain using a 16-channel transceiver coil at 7T. Magn Reson Med. 2013;69(5):1285-96.
Zhang, et al., Imaging electric properties of biological tissues by RF field mapping in MRI. IEEE Trans Med Imaging. 2010;29(2):474-81.
Zhou, et al. "Amide proton transfer (APT) contrast for imaging of brain tumors." Magnetic Resonance in Medicine: An Official Journal of the International Society for Magnetic Resonance in Medicine 50.6 (2003): 1120-1126.
International Search Report and Written Opinion. Issued by the International Searching Authority (ISA/US) in application No. PCT/US2018/014365 dated May 17, 2018. 10 pages.

(56) References Cited

OTHER PUBLICATIONS

Leitao, et al., "Absolute phase image reconstruction: a stochastic nonlinear filtering approach." IEEE Transactions on Image Processing 7.6 (1998): 868-882.

* cited by examiner

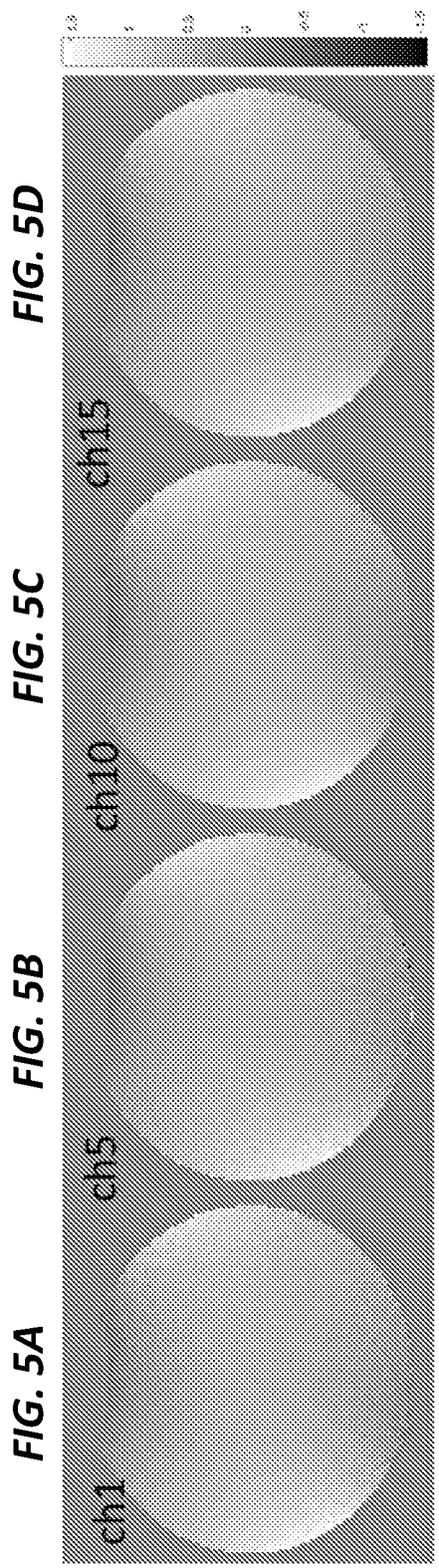

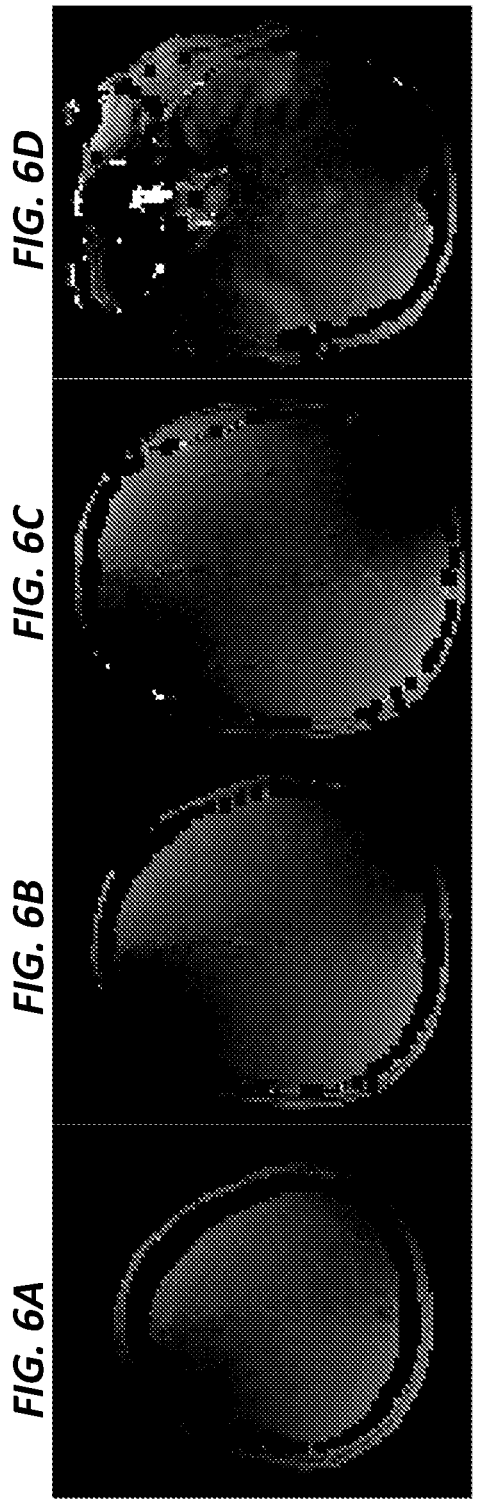

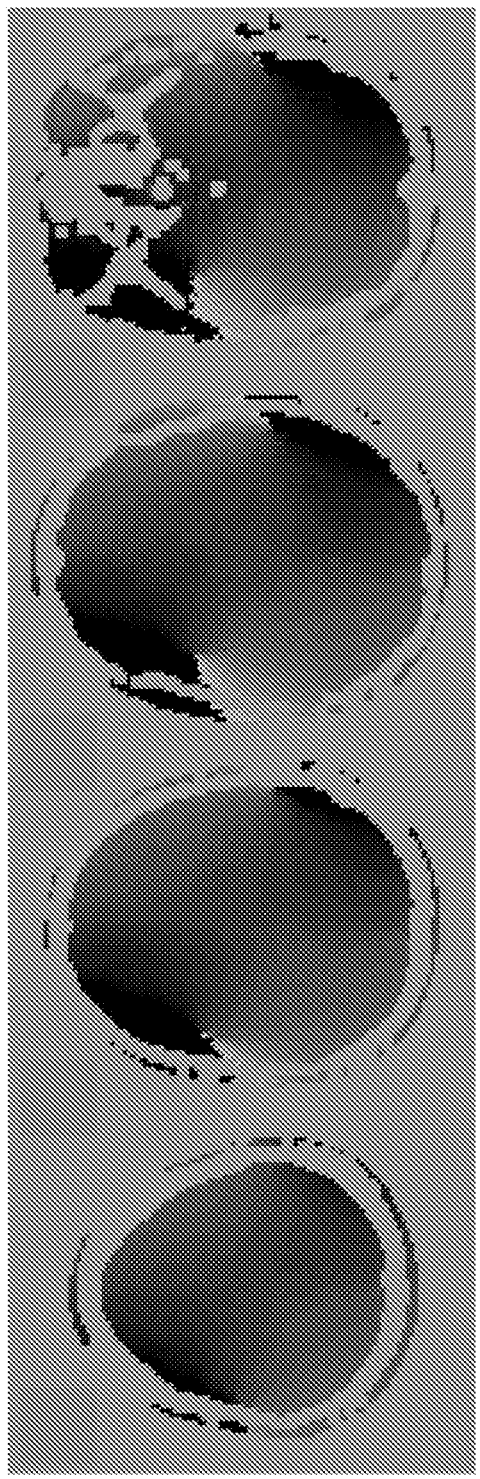

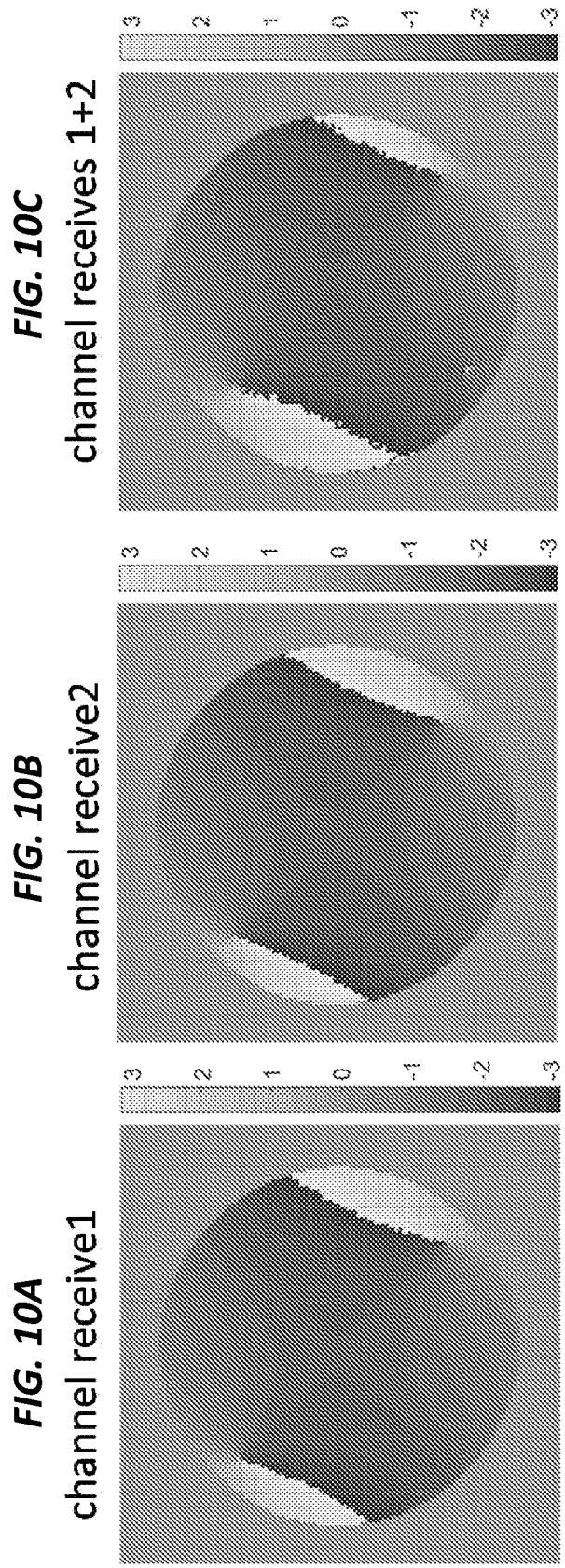
FIG. 10A channel receive1
FIG. 10B channel receive2
FIG. 10C channel receives 1+2

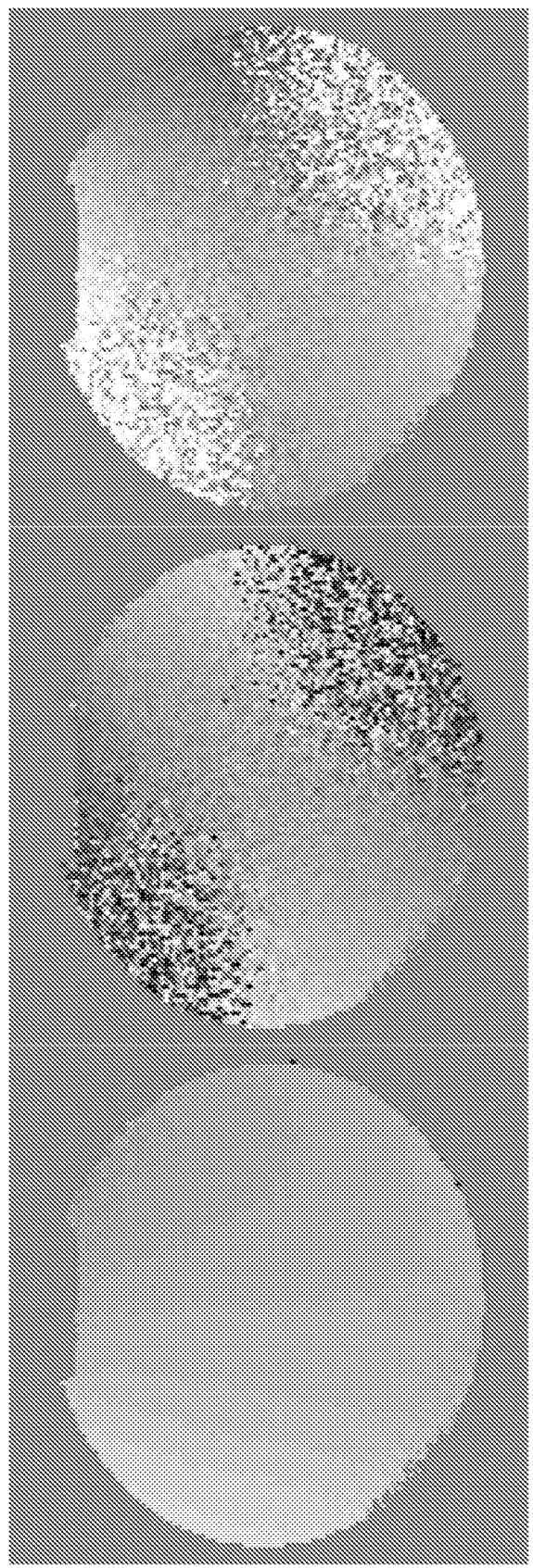

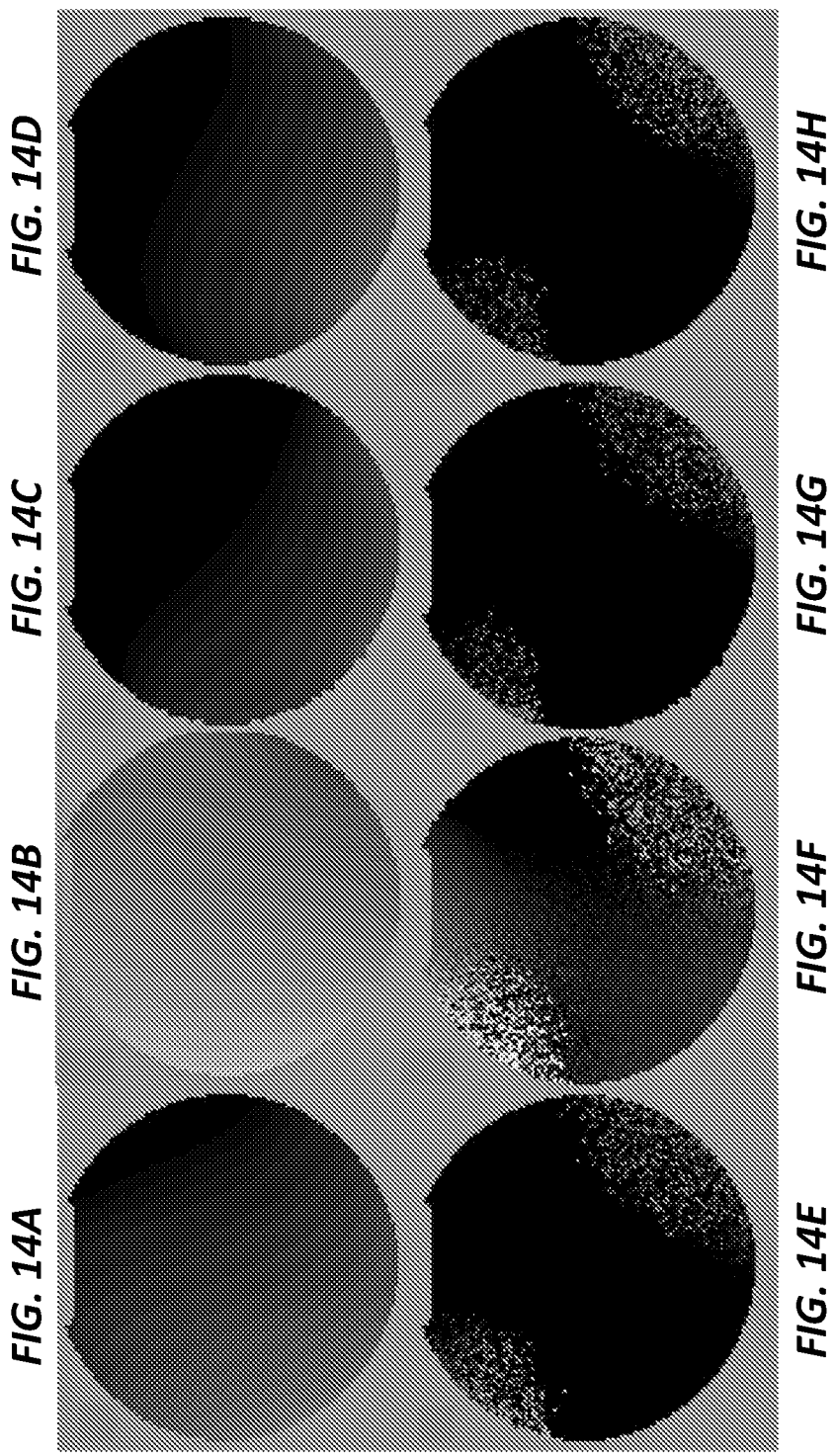

ESTIMATING ABSOLUTE PHASE OF RADIO FREQUENCY FIELDS OF TRANSMIT AND RECEIVE COILS IN A MAGNETIC RESONANCE

CROSS-REFERENCE TO RELATED APPLICATIONS

This application is a national stage application filed under 35 U.S.C. 071 of PCT/US2018/014365 filed Jan. 19, 2018, which claims the benefit of U.S. Provisional Patent Application No. 62/448,116, filed on Jan. 19, 2017, entitled "METHODS AND SYSTEMS FOR ESTIMATING ABSOLUTE PHASE OF RADIOFREQUENCY FIELDS OF TRANSMIT AND RECEIVE COILS IN A MAGNETIC RESONANCE IMAGING (MM) SYSTEM," the disclosures of which are expressly incorporated herein by reference in their entireties.

BACKGROUND

Estimating absolute phase and magnitude of radiofrequency (RF) field including both transmit field ($B_1^+$) and receive sensitivity ($B_1^-$) is important for various stages of the magnetic resonance imaging (MRI) procedure. For example, RF transmit field ($B_1^+$) and/or RF receive sensitivity ($B_1^-$) can be used for image combination, RF shimming, parallel imaging reconstruction, electric property tomography (EPT), MRI RF safety, application in magnetoencephalography (MEG) [Cohen D., Magnetoencephalography: Evidence of magnetic fields produced by alpha rhythm currents, 1972; 161:664-666], and Electroencephalography (EEG) [Caton R., The electric current of the brain, Br Med J., 1875; 2:278-296].

The spatial absolute phase information is important in various stages of MRI scanning: (1) coil design and RF safety [Katscher et al., IEEE transactions on medical imaging, 2009; 28:1365-1374]; (2) transmit shimming and/or parallel transmit [Padormo et al., NMR in Biomedicine 2016; 29:1145-1161]; (3) parallel image reconstruction including magnitude image and/or phase image [Kim et al. Magn Reson Med 2016 in publication; Dagher J and Nael K., Magn Reson Med 2016; 75:1218-1231]; (4) the combination of MR image or MR spectroscopy from each element of multiple receivers [Rodgers C T and Robson M D., Magn Reson Med 201675:473-487]; (5) exploration of new contrast and biomarker, such as susceptibility-weighted imaging [Duyn et al., Proc Natl Acad Sci USA 2007; 104:11796-11801], susceptibility tensor imaging, in vivo conductivity [Zhang et al., IEEE reviews in biomedical engineering 2014; 7:87-96]; (6) quantitative MRI and magnetic resonance spectroscopy (MRS), such as quantitative susceptibility mapping (QSM) [Li et al., Neuroimage 2011; 55:1645-1656], temperature and encode flow velocity[Peng et al., Magn Reson Med 2010; 64:472-480].

Generally, acceleration factors of 2 or 3 are applied during clinical routine scans. Higher acceleration factors are not reached because of two factors. First, the signal-to-noise ratio (SNR) is reduced by the square root of the acceleration factor because of the reduced amount of k-space samples. Secondly, noise is amplified during the image reconstruction process. Noise amplification originates from image reconstruction process as an inverse problem [Blaimer M et al., Magn Reson Med 2016; 75:1086-1099]. But noise amplification can be reduced by applying phase-constrained parallel MRI algorithms. In these algorithms, a phase distribution correction is performed during the reconstruction process. The phase distribution directly influences the reconstruction quality. In other words, both coil sensitivity profiles as well as spatial phase distribution contribute to the image quality of phase-constrained parallel MRI methods. There are two existing approaches for phase-constrained parallel MRI: (1) a phase-constrained method in image domain, such as a phase-constrained sensitivity encoding (PC-SENSE) [Lew et al., Magn Reson Med 2007; 58: 910-921] and (2) a conjugate k-space symmetry method, such as generalized autocalibrating partially parallel acquisitions (GRAPPA) [Griswold et al., Magn Reson Med 2002; 47: 1202-1210], SPIRiT [Lustig M and Pauly J M., Magn Reson Med 2010; 64:457-471] or ESPIRiT [Lustig M et al., Magn Reson Med 2014; 71:990-1001]. The phase information for these approaches is based on additional virtual coils. In addition, the phase information is relative phase information. The spatial phase information is not accurate and influences the image quality for phase-constrained parallel MRI methods.

Signals of magnetic resonance image and magnetic resonance spectroscopy from multiple receiver coils can be combined to maximize the signal-to-noise ratio (SNR) using known receive sensitivity and noise covariance [Roemer et al., Magn Reson Med 1990; 16: 192-225]. The Biot-Savart law or phantom replacement has been used to estimate complex receive sensitivity for coil combination, saturation correction, or sensitivity correction. But, these approaches are awkward and inaccurate for coil combination in vivo. [Rodgers et al., Magn Reson Med 2016; 75:473-487].

U.S. Pat. No. 8,891,846 to Fautz discloses a method for phase correction of K-space data generated using a magnetic resonance tomography device. The resulting magnitudes and phase of $B1^+$ field may be adjusted using the phases and magnitudes of each individual transmitter (RF shimming). Accurate estimation of phases and magnitudes of the $B1^+$ maps for each RF coil is necessary to achieve simultaneous excitation for RF shimming.

Parallel imaging techniques rely on the linear superposition of the electromagnetic fields produced by the individual coils or coil elements of the MRI system. For most applications, the distribution of RF field produced by each coil or element must be known in magnitude and phase at least relatively to that of the other channels. For example, the coil sensitivities of the receivers must be known for image combination of signals from each coil or coil element. In Magn. Reson. Med. 1990; 16: 192-225, Roemer P B et al. discloses an image combination method of complex signals from each coil in a phased array based on uniform noise and uniform receive sensitivity. In Magnetic Resonance in Medicine 2016; 76:1730-1740, David O Brunner and Klaas P Pruessmann disclose an image combination method based on the relative sensitivities of the transmitters and receivers using for imaging.

Parallel imaging allows the reconstruction of images from under-sampled multi-receiver coil data. The two main approaches are: SENSE, which explicitly uses information of the phases and magnitudes of receiver coil sensitivities, and GRAPPA, which makes use of learned correlations in k-space. In Magn Reson Med 2014; 71:990-1001, Uecker M et al. discloses a method to obtain highly accurate estimations of the coil sensitivities from a fully-sampled calibration region in the k-space center. However, the low frequency information from transmit coil will be added in k-space center, which then influences the accuracy of estimating complex (i.e. magnitude and phase) receiver coil sensitivities.

In order to determine the distribution of specific absorption rate (SAR) in biological tissues exposed to RF energy, accurate knowledge of dielectric properties of the tissues is essential. A survey of the literature showed that most of the research on dielectric properties of biological samples was done on non-living tissue. Regarding brain tissue, which is of special interest due to the exposure of the human head from modern handheld communication devices, most work was done in vitro on various animal tissues. Although the currently available data have been generally accepted, there is reason to ask whether the dielectric properties of living human tissue are reliably reflected by these data. It is possible that the electric conductivity of living brain tissue might differ significantly from values commonly used today in RF dosimetry [Schmid G, Neubauer G, Mazal P R. Dielectric properties of human brain tissue measured less than 10 hour postmortem at frequencies from 800 to 2450 MHz. Bioelectromagnetics. 2003; 24:423-30]. Therefore, accurate estimation of electric properties (e.g., conductivity and permittivity) is important to calculate the SAR and evaluate the RF safety of MR scanning. EPT can be used to obtain patient-specific values of the electric properties. As the electric properties, for example, depend on age and are affected by pathological changes, the use of personalized properties will reduce the uncertainty. Ideally, the EPT maps can directly be used as an input for electromagnetic simulations. Similarly, the use of personalized properties can improve the accuracy of source localization in MEG and EEG. Additionally, various interventions, such as transcranial magnetic stimulation (TMS) or RF ablation, can benefit from individualized estimation of electrical properties.

U.S. Pat. No. 9,229,074 to Voigt discloses that local specific SAR is based on an electric property and the mass density of a segmented geometry of an object. The electric property is estimated by magnitude and absolute phase of $B_1^+$. Additionally, EPT is a recently introduced technique to reconstruct conductivity and permittivity from measurable radio frequency (RF) magnetic field maps. In Phys. Med. Biol. 1991; 36:723-734, Haacke et al. disclose that EPT can be estimated by quantitative MRI method. In Magn. Reson. Med. 2011; 66:456-466, Voigt T et al. discloses a method for quantitative conductivity and permittivity imaging of the human brain using EPT.

In Magnetic resonance in medicine 2017; 77:1201-1207, Uecker, M et al disclosed a virtual conjugate coil method to determine the background phase accurately and robustly according to conjugate symmetry in k-space. Although the virtual coil is very useful for phase-constrained image reconstruction, the estimated phase is not the absolute phase, but background phase. In most cases, the background phase is completely different from the absolute phase of receive coil or array coils. Thus, replacing the absolute phase with background phase in MRI system may introduce a significant error.

In Magnetic Resonance in Medicine, 2002; 47:529-538, McKenzie, C. A., et al. discloses a self-calibrating method for complex coil sensitivity. The phase information of receive sensitivity is also extracted by auto-calibration in parallel MRI reconstructions. The calibration method implements fully sampled central k-space lines to determine the complex coil sensitivity. But the central k-space include all low-spatial-frequency components including transmit field, object being imaged, and coil sensitivity. This method therefore assumes that the contribution from other factors to central k-space is ignorable and coil sensitivity is dominant. The assumption is not available in most cases.

In IEEE Trans. Med. Imag., 2009; volume 28: p 1365-1374, Katscher et al. discloses a transceiver phase assumption that the absolute transmit phase of a quadrature volume coil can be a half of the transceiver phase. The disclosure is only directed to a transceiver coil.

U.S. Patent Application 2014/0300354 to He et al. discloses that a $B_1^+$ absolute phase distribution from the derived $B_1^+$ magnitude maps and $B_1^+$ relative phase maps; and a $B_1^-$ absolute phase distribution from the derived $B_1^-$ magnitude maps and $B_1^-$ relative phase maps.

U.S. Patent application 2016/0054262 to Sodickson et al. discloses that the absolute phase distribution of the RF magnetic field can generally be considered to be fundamentally inaccessible due to the nature of signal excitation and detection in magnetic resonance. Sodickson discloses an approximation method (e.g. a Local Maxwell Tomography approach) to estimate the absolute phase.

SUMMARY

An example method for determining spatial distribution of an absolute phase of radio frequency (RF) transmit field $B_1^+$ in a magnetic resonance imaging (MRI) system is described herein. The method can include selecting a transmit coil for which to measure the absolute phase of the RF transmit field $B_1^+$, exciting nuclear spins in magnetic resonance (MR) nuclei using at least two transmit configurations of the transmit coil, and detecting first MR signals and second MR signals arising from exciting nuclear spins in MR nuclei using a first transmit configuration and a second transmit configuration, respectively. The method can also include acquiring a first set of complex k-space data and a second set of complex k-space data from the first MR signals and the second MR signals, respectively, and estimating an absolute phase $B_1^+$ map of the transmit coil using the first set of complex k-space data and the second set of complex k-space data.

Additionally, the method can optionally further include transforming the first set of complex k-space data and the second set of complex k-space data into a first image and a second image, respectively. The absolute phase $B_1^+$ map of the transmit coil can be estimated using the first image and the second image.

Alternatively or additionally, the transmit coil can be a surface coil, a transmit coil element, an array of transmit coil elements, or a volume coil.

Alternatively or additionally, the at least two transmit configurations can include at least two different transmit coil configurations. For example, the different transmit configurations can include, but are not limited to, an array of transmit coil elements and a quadrature transmit volume coil.

Alternatively or additionally, the at least two transmit configurations can include at least two different transmit coil surface coils or elements or at least two different arrays of transmit coil elements. For example, dual transmit coils can be formed by two volume coils.

Alternatively or additionally, the at least two transmit configurations can include an identical hardware configuration (e.g., the same one or more transmit coil elements) with different phases of the identical hardware configuration.

Alternatively or additionally, the method can optionally further include estimating the absolute phase $B_1^+$ map of the transmit coil using the first set of complex k-space data and the second set of complex k-space data.

Alternatively or additionally, the method can optionally further include estimating an absolute phase of $B_1^+$ transmit field for an arbitrary transmit coil using the absolute phase $B_1^+$ map of the transmit coil as a reference.

Alternatively or additionally, the method can optionally further include applying the absolute phase $B_1^+$ map of the transmit coil to improve image quality of simultaneous multi-slice excitation.

Alternatively or additionally, the method can optionally further include applying the absolute phase $B_1^+$ map of the transmit coil to improve performance of RF shimming and/or parallel transmit field.

Alternatively or additionally, the method can optionally further include applying the absolute phase $B_1^+$ map of the transmit coil to estimate changes of electromagnetic field caused by an electromagnetic property of an object being imaged. The electromagnetic property can include, but is not limited to, at least one conductivity and/or permittivity.

Alternatively or additionally, the method can optionally further include estimating an absolute phase of $B_1^-$ field of a receive coil using the absolute phase $B_1^+$ map of the transmit coil and at least one phase image.

Alternatively or additionally, the method can optionally further include combining with various fast imaging techniques at least one of parallel imaging acquisition, undersampling acquisition, compensate sense, or simultaneous multiple-slice excitation, to reduce a scanning time for estimating the absolute phase $B_1^+$ map of the transmit coil.

Alternatively or additionally, the estimation of the absolute phase $B_1^+$ map of the transmit coil provides information associating an estimated electrical property with a pathological state of tissues in a subject.

Alternatively or additionally, the method can optionally further include combining with various image sequences and techniques at least one of gradient echo-based sequences, spin-echo-based sequences, echo planar imaging (EPI)-based sequences, or ultra-short echo time sequences, to reduce or remove the effect of $B_0$ inhomogeneity on the absolute phase $B_1^+$ map of the transmit coil.

Alternatively or additionally, the method can optionally further include determining local specific energy absorption rate (SAR) using the absolute phase $B_1^+$ map of the transmit coil.

Alternatively or additionally, the absolute phase $B_1^+$ map of the transmit coil can be used to improve image quality and increase accelerator factors for at least one of multiple transmit coil, multiband excitation, or multiple receive coil imaging techniques.

An example magnetic resonance imaging (MRI) system for determining spatial distribution of an absolute phase of radio frequency (RF) transmit field $B_1^+$ of a transmit coil is also described herein. The MRI system can include a transmitting and receiving unit comprising at least one RF coil and an MRI system controller operably coupled with the transmitting and receiving unit. The transmitting and receiving unit can be configured to excite nuclear spins in magnetic resonance (MR) nuclei using at least two transmit configurations using the at least one RF coil, and detect first MR signals and second MR signals using the at least one RF coil, wherein the first MR signals and second MR signals arise from exciting nuclear spins in MR nuclei using a first transmit configuration and a second transmit configuration, respectively. The MRI system controller can be configured to acquire a first set of complex k-space data and a second set of complex k-space data from the first MR signals and the second MR signals, respectively, transform the first set of complex k-space data and the second set of complex k-space data into a first image and a second image, respectively, and estimate an absolute phase $B_1^+$ map of the transmit coil using the first image and the second image.

An example method for determining spatial distribution of an absolute phase of radio frequency (RF) receive field $B_1^-$ in a magnetic resonance imaging (MRI) system is also described herein. The method can include exciting nuclear spins in magnetic resonance (MR) nuclei using a transmit coil of the MRI system, detecting MR signals arising from exciting nuclear spins in MR nuclei using a receive coil of the MRI system, acquiring a complex image (e.g., complex k-space data) from the MR signals, and estimating a phase of the complex image. The method can also include receiving an absolute phase $B_1^+$ map of the transmit coil of the MRI system, and estimating an absolute phase of $B_1^-$ field of the receive coil using the absolute phase $B_1^+$ map of the transmit coil of the MRI system and the phase of the complex image.

Alternatively or additionally, the method can further include receiving an inhomogeneous $B_0$ map, and the absolute phase of $B_1^-$ field of the receive coil is estimated using the absolute phase $B_1^+$ map of the transmit coil of the MRI system, the phase of the complex image, and the inhomogeneous $B_0$ map. It should be understood that the $B_0$ map is an additional complex image.

Alternatively or additionally, the complex image can be the same complex image used for estimating the absolute phase $B_1^+$ map of the transmit coil of the MRI system.

Alternatively or additionally, the complex image can be a different complex image than that used for estimating the absolute phase $B_1^+$ map of the transmit coil of the MRI system.

Alternatively or additionally, the method can optionally further include applying the absolute phase of $B_1^-$ field of the receive coil to improve image quality of both magnitude image and phase image from parallel image reconstruction.

Alternatively or additionally, the method can optionally further include applying the absolute phase of $B_1^-$ field of the receive coil to estimate changes of electromagnetic field caused by an electromagnetic property of an object being imaged.

Alternatively or additionally, the method can optionally further include applying the absolute phase of $B_1^-$ field of the receive coil to improve the quality of both image and spectroscopy signal combination from each receive channel.

Alternatively or additionally, the method can optionally further include applying the absolute phase of $B_1^-$ field of the receive coil to improve the qualitative image and qualitative spectroscopy.

Alternatively or additionally, the method can optionally further include combining with various fast imaging techniques at least one of parallel imaging acquisition, undersampling acquisition, compensate sense, or simultaneous multiple-slice excitation, to reduce a scanning time for estimating the absolute phase of $B_1^-$ field of the receive coil.

Alternatively or additionally, the estimation of the absolute phase of $B_1^-$ field of the receive coil provides information associating an estimated electrical property with a pathological state of tissues in a subject.

Alternatively or additionally, the method can optionally further include combining with various image sequences and techniques at least one of gradient echo-based sequences, spin-echo-based sequences, echo planar imaging (EPI)-based sequences, or ultra-short echo time sequences, to reduce or remove the effect of $B_0$ inhomogeneity on the absolute phase of $B_1^-$ field of the receive coil.

Alternatively or additionally, the method can optionally further include determining local specific energy absorption rate (SAR) using the absolute phase of $B_1^-$ field of the receive coil.

Alternatively or additionally, the method can optionally be used to improve image quality and increase accelerator factors for at least one of multiple transmit coil, multiband excitation, multiple receive coil imaging techniques using the absolute phase map of $B_1^+$ of transmit coil and/or the absolute phase of $B_1^-$ field of the receive coil.

An example magnetic resonance imaging (MRI) system for determining spatial distribution of an absolute phase of radio frequency (RF) transmit field $B_1^-$ of a receive coil is also described herein. The MRI system can include a transmitting and receiving unit comprising at least one RF coil. The transmitting and receiving unit is configured to excite nuclear spins in magnetic resonance (MR) nuclei, and detect MR signals arising from exciting nuclear spins in MR nuclei using the at least one RF coil. The MRI system can also include an MRI system controller operably coupled with the transmitting and receiving unit. The MRI system controller can be configured to: acquire a complex image from the MR signals; estimate a phase of the complex image; receive an absolute phase $B_1^+$ map of the transmit coil; and estimate an absolute phase of $B_1^-$ field of a receive coil using the absolute phase $B_1^+$ map of the transmit coil and at least one of the complex image or the phase of the complex image.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 3D-3F are absolute phase images of a transceiver birdcage coil with linear driven phase (FIG. 3D), quadrature driven phase (FIG. 3E), and reverse quadrature driven phase (FIG. 3F), respectively, which are estimated from the phase images shown in FIGS. 3A-3C, respectively.

FIGS. 5A-5D illustrate estimation of absolute phase of $B_{1,t}^+$ of dual quadrature driven transmit coils with a spherical phantom using phase images acquired with both each individual coil and their combination. In FIGS. 5A-5D, the receive coil is a 20 channel head coil. FIG. 5A is the image corresponding to receive channel 1. FIG. 5B is the image corresponding to receive channel 5. FIG. 5C is the image corresponding to receive channel 10. FIG. 5D is the image corresponding to receive channel 15. The combined dual transmit coil is driven with quadrature phase (i.e., coil element 1 with phase of 0 degree and coil element 2 with phase of 90 degree). The absolute phase of quadrature-driven dual transmit coil is equal to the absolute phase superposition of both coil elements 1 and 2. The absolute phase of coil element 1 is estimated using subtraction of phase images acquired respectively with the dual transmit coil and coil element 2. Similarly, the absolute phase of coil element 2 is estimated using subtraction of phase images acquired respectively with the dual transmit coil and coil element 1.

FIGS. 6A-6D illustrate estimation of absolute phase of $B_{1,t}^+$ of dual quadrature driven transmit coils with a volunteer brain (e.g., in vivo imaging) at the different axial slices using the technique described with regard to FIGS. 5A-5D.

In FIGS. 7A-7D, the receive coil is a 20 channel head coil. FIG. 7A is the image corresponding to receive channel 1. FIG. 7B is the image corresponding to receive channel 5. FIG. 7C is the image corresponding to receive channel 10. FIG. 7D is the image corresponding to receive channel 15. The dual transmit coil is driven with quadrature phase (i.e., coil element 1 with phase of 0 degree and coil element 2 with phase of 90 degree). Similar to FIGS. 3A-3F, the absolute phase of quadrature-driven dual transmit coil is obtained by subtraction of two phase images acquired with dual transmit coil with linear driven phase and reverse quadrature driven phase. The absolute phase of $B_1^+$ of dual transmit coils can be estimated using the method described in FIGS. 3A-3F. Theoretically, the measured absolute phase of $B_1^+$ in FIGS. 7A-7D should be identical to those of FIGS. 5A-5D. However, there exist a significant difference. The reason results from the coupling between transmit coil element 1 and transmit coil element 2.

FIGS. 8A-8D illustrate estimation of absolute phase of $B_1^+$ of dual transmit coils with a volunteer brain (e.g., in vivo imaging) using the method described with regard to FIGS. 7A-7D.

FIGS. 10A-10C illustrate estimation of absolute phase of $B_1^+$ of dual transmit coils as a quadrature transceiver coil with a spherical phantom according to an implementation described herein. FIGS. 10A-10C illustrate absolute phase of $B_1^+$ estimated from phase images acquired with receive channel 1 (FIG. 10A), receive channel 2 (FIG. 10B), and their combination (FIG. 10C).

FIGS. 12A-12C illustrate a comparison of absolute phase of $B_{1,t}^+$ mapping and $B_{1,r}^-$ mapping for a transceiver coil with a spherical phantom.

FIGS. 14A-14H illustrate the phase images (FIGS. 14A-14D) of a spherical phantom acquired with a quadrature dual transmit coil and absolute receive phases (FIGS. 14E-14H) of 16 channel head receive coil array.

DETAILED DESCRIPTION

Figure 1A:
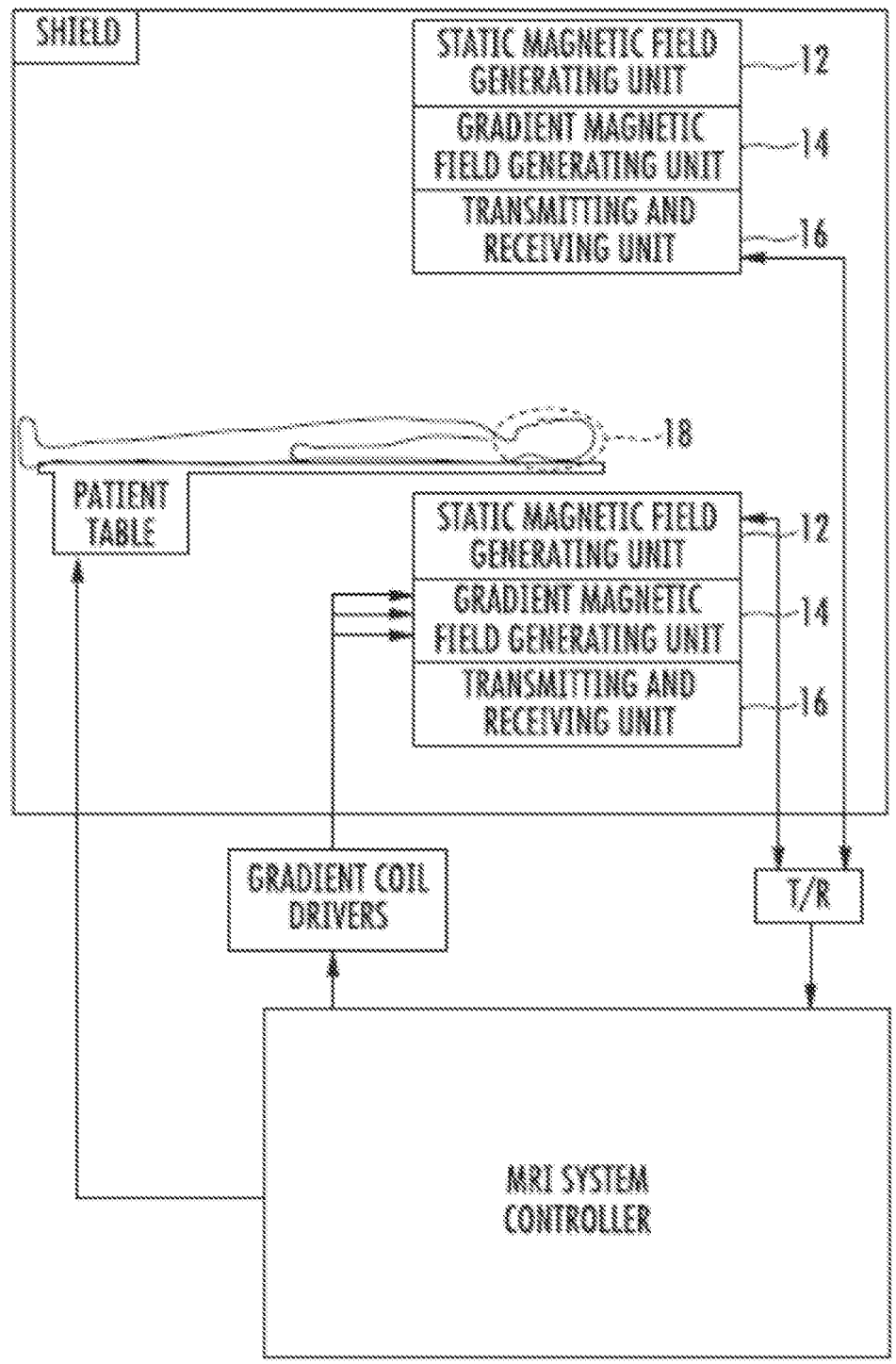
FIG. 1A is a diagram illustrating an example MRI system.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for determining spatial distribution of an absolute phase of RF transmit field $B_1^+$ and/or RF receive field $B_1^-$ in an MRI system, it will become evident to those skilled in the art that the implementations are not limited thereto.

Definitions

Coil performance of transmit coil and/or receive coil includes, but not limited to, uniformity of radiofrequency field and received signal intensity.

Image quality includes, but is not limited to, signal-to-noise ratio and its variations, contrast-to-noise and its variations, artifacts, and accuracy. Accuracy is a metric indicating the difference between an acquired image and an image as a ground truth, or a difference between a result and a "true" value.

Radiofrequency field $B_1$ indicates $B_{1,t}$ from a transmit coil and $B_{1,r}$ from a receive coil.

A transceiver coil is a RF coil which is used for both transmission and reception without any hardware configuration change.

$B_{1,t}$ is the transmit RF field which is generated by a transmit coil in MRI system.

$B_{1,r}$ is the receiver RF field which is generated by a receiver coil in MRI system.

$B_1^+$ is the positive circularly polarized component of a transversal transmit field of a RF pulse which is generated by a transmit coil. The RF pulse can be used as an excitation RF pulse, refocused RF pulse, and magnetization preparation RF pulse. The transmit coil can be at least one of volume coil, surface coil, one element of an array coils, or a combination thereof. The transversal transmit RF field can be decomposed into two rotating fields: the positive circularly polarized component $B_1^+$, which rotates in the direction of nuclear magnetic moment precession (counterclockwise direction), and the negative circularly polarized component $B_{1,t}^-$, which rotates opposite to the direction of precession (clockwise direction). In an MRI system, only the positive circularly polarized component of the transmitting field $B_{1,t}^+$ contributes to the excitation of proton nuclei spins. Therefore, $B_1^+$ is sometimes used herein to refer to the transmit field of a transmit coil (e.g., the RF transmit field $B_1^+$ of a transmit coil).

$B_{1,r}^-$ is the negative circularly polarized component of a transversal receiver field of a receive coil. Similar to $B_1^+$, the transversal receiver field can be decomposed into two rotating fields: the positive circularly polarized component $B_{1,r}^+$ which rotates in the direction of nuclear magnetic moment precession (counterclockwise direction), and the negative circularly polarized component $B_{1,r}^-$, which rotates opposite to the direction of precession (clockwise direction). In an MRI system, the receiver sensitivity of proton nuclei spins is proportional to the negative circularly polarized component of the transmitting field $B_{1,r}^-$. Therefore, $B_1^-$ is sometimes used herein to refer to the receiver sensitivity of a receiver coil (e.g., the RF receive field $B_1^-$ of a receive coil).

An absolute phase of a transmit field $B_{1,t}$ can be defined as a phase of the transmit field $B_{1,t}$ at the zero point of time, which is relative to the phase independent of spatial location.

An absolute phase of receive field $B_{1,r}$ can be defined as a phase of the receive field $B_{1,r}$ at the zero point of time, which is relative to the phase independent of spatial location.

$B_1$ field mapping includes both transmit field mapping $B_{1,t}$ of a transmit coil (e.g., RF transmit field of a transmit coil $B_1^-$) and receiver sensitivity mapping $B_{1,r}$ mapping of a receiver coil (e.g., RF receive field of a receive coil $B_1^-$). It should be understood that the MRI systems described herein can include a plurality of transmit coils and/or a plurality of receiver coils. Optionally, the transmit or receiver coils can be an array coil (e.g., transmit coil elements arranged in an array or receiver coil elements arranged in an array). In some implementations, the transmit and receiver coils are different coils. In other implementations, the transmit and receiver coil are the same coil (e.g., a transceiver coil). Alternatively or additionally, the transmit coil can include, but is not limited to, a transmit volume coil, a transmit surface coil, or an array coil. The absolute phase of $B_1^+$ map described herein can be an absolute phase $B_1^+$ map of a portion of the, or the entire, transmit coil or element of an array coil. Alternatively or additionally, the receiver coil can include, but is not limited to, a receiver coil or an array coil. The absolute phase $B_1^-$ map described herein can be an absolute phase $B_1^-$ map of a portion of the, or the entire, receiver coil or element of an array coil.

Absolute Phase Mapping of B1 Overview

Absolute phase estimation of $B_1$ field can be significant to applications including, but not limited to, image quality improvement, RF safety, RF coil design and optimization, quantitative MRI, RF shimming, tailored RF shimming, parallel transmit field, parallel image reconstruction, parallel image combination, phase image reconstruction and electromagnetic property tomography.

Either inhomogeneous transmit or inhomogeneous receiver sensitivity or both can gives rise to signal and contrast inhomogeneities in the reconstructed images. Without removing or sufficiently reducing these $B_1$ inhomogeneities, the value of MRI images in clinic and research may be compromised.

$B_1$ estimation can also be important for RF safety in high field and ultra-high field MRI. $B_1$ inhomogeneities will generate a local exposure where most of the absorbed energy is applied to one body region rather than the entire body. As a result, the hotspots may occur in the exposed tissues and may lead to regional damage of these tissues even when global SAR is less than U S Food and Drug Administration (FDA) and International Electrotechnical Commission (IEC) SAR limits.

Absolute phase estimation of $B_1$ field can also be important for RF coil design. The uniformity of $B_1$ field is important metric for RF coil design and optimization. The current phase of each coil element can influence absolute phase of entire coil $B_1$ field, and then influence the uniformity of B1 field. As for specific application RF coil, such as knee coil, breast coil, the RF inhomogeneity should be greatly improved if the loaded effect is taken account into the coil design. The absolute phase of $B_1$ field associates with the electromagnetic properties of the loaded.

Absolute phase of both transmit field and receiver sensitivity can also be important for quantitative MRI, such as quantitative fast $T_1$ mapping and MR image segmentation. It is known that contrast-to-noise ratio and signal inhomogeneity are major reasons which strong affect the performance of segmentation. In quantitative MRI, one solution is to measure an absolute $B_1^+$ and $B_1^-$ maps and correct the intensity inhomogeneities that arise from $B_1^+$ and/or $B_1^-$ variations.

Absolute phase of both transmit field $B_1^+$ and receiver sensitivity $B_1^-$ can provide the information about coil performance and inhomogeneity and be used for preventive maintenance of RF system, including transmit coil and/or receiver coil system.

RF shimming, tailored RF shimming and parallel transmission are techniques that enable high field and ultra-high field MRI at maximum image quality and RF patient safety. These techniques are based on accurate absolute phase of $B_1^+$ mapping and adjust current amplitude and phase of each element of the RF coils and/or gradient configuration to maximize $B_1^+$ or flip angle uniformity in subsequent imaging. The estimation of transmit field is precondition of RF shimming and parallel transit techniques. RF shimming technique is coil configuration and object dependent. Thus, the transmit field must be estimated for each coil and object in RF shimming technique. Reducing time for estimating transmit field will reduce the time of applying RF shimming technique in clinical setting. Additionally, parallel transmit technique is coil configuration, object and sequence dependent. Therefore, the transmit field must be estimated for each coil, object and sequence in parallel transmit technique. Reducing time for estimating transmit field reduces the time of applying parallel transmit technique in clinical setting. The estimation of transmit field is precondition of RF shimming and parallel transit techniques.

Absolute phase of both transmit field and receiver sensitivity has an increasing role in electrical property tomography. For example, the conductivity and permittivity of living issues can be directly estimated using the absolute phase mapping of $B_1$. U.S. 2014/0103925 to Hancu et al. proposes a method in which the complex phase of a specific image is proportional to the product of the transmit radio frequency magnetic field and the receive RF magnetic field for a transceiver coil to simplify the symmetry assumption of transceiver phase.

The current state-of-the-art methods of absolute phase estimation are not accurate because absolute phase is estimated using approximations. For example, Birdcage coil; Multi-transmit coil. Therefore, the conventional methods for estimating absolute phase of a transmit coil is available only for specific transmit coil systems (i.e., birdcage transceiver coil and special multi-transmit). The absolute phase of a birdcage transceiver coil is based on symmetry assumption [Zhang X, Liu J, He B. Magnetic-resonance-based electrical properties tomography: a review, IEEE reviews in biomedical engineering 2014; 7:87-96]. van Lier et al indicates that the symmetry assumption can introduce error in the estimation of absolute phase [van Lier et al. Magn Reson Med 2014; 71:354-363]. Moreover, the relative phase method described in U.S. 2014/0300354 to He et al. is relative to a phase dependent of spatial location. This may be fine for image reconstruction but may be unacceptable for local SAR estimation. U.S. 20160054262 to Sodickson et al. proposes local Maxwell tomography technique to estimate absolute reference phase and magnetization from a sufficient number of transmit and receive coil elements. However, it requires specific hardware configuration of a sufficient number of transmit and receive coil elements.

Auto-calibration methods have also been used to estimate absolute phase of receiver sensitivity for parallel imaging reconstruction because coil sensitivity varies slowly and smoothly over space. The auto-calibration methods have some drawbacks, although they are good for parallel imaging reconstruction. Receiver sensitivity is a property of the receiver coil, independent of transmit coil, acquisition sequence, and imaging parameters. But receiver sensitivity estimated using the auto-calibration methods depends tremendously on these factors, indicating the inaccuracy of the method. This is because all calibration methods introduce a virtual receiver coil whose receiver sensitivity is equal to the square root of the sum of the squares of receiver sensitivity of each coil element, and assume that the sensitivity of the virtual coil is uniform. In practice, this assumption is problematic, particularly at high field strengths and if the imaged object is of a large size. The errors in estimated receiver sensitivity using auto-calibration methods are not problematic for qualitative parallel image reconstruction because artifacts of reconstruction are dominated by relative receiver sensitivity. However, they are problematic for quantitative parallel image reconstruction or quantitative MRI using internal and external references. In addition, the auto-calibration methods also require additional scan time to obtain additional reference k-space line(s).

All of these above mentioned methods for absolute phase of $B_{1,t}^+$ mapping are available for specific transmit coil configurations. Some methods are based on the assumption of symmetric transceiver phase [Zhang X, Liu J, He B. Magnetic-resonance-based electrical properties tomography: a review, IEEE reviews in biomedical engineering 2014; 7:87-96], leading to the inaccuracy of absolute phase estimation. Additionally, the absolute phase derived from multichannel transmit coil array requires specific hardware—multi-transmit coil array.

All of these above mentioned $B_{1,r}^-$ mapping methods deal only with either the phase of $B_{1,r}^-$ related to a virtual receiver coil or a reference receiver coil. In other words, none of the above mentioned $B_{1,r}^-$ mapping methods deal with the absolute phase of $B_{1,r}^-$. For example, the phase information of $B_{1,r}^-$ is important for image reconstruction and image combination of images from different coils or coil elements.

MRI System Overview

An example MRI system is described in U.S. Pat. No. 8,502,538 to Dannels et al., entitled "$B_1$ and/or $B_0$ mapping in MRI system using k-space spatial frequency domain filtering with complex pixel by pixel off-resonance phase in the $B_0$ map," issued Aug. 6, 2013, the disclosure of which is hereby incorporated by reference in its entirety. The example MRI system is described below with reference to FIG. 1A. This disclosure contemplates that the techniques for determining spatial distribution of an absolute phase of RF transmit field $B_1^+$ and/or RF receive field $B_1^-$ can optionally be implemented using the example MRI system. For example, the MRI system shown in FIG. 1A has a static magnetic field generating unit 12 and a gradient magnetic field generating unit 14 for generating respective magnetic fields in proximity to an object 18. The MRI system also includes a transmitting and receiving unit 16 for irradiating RF pulses to the object and receiving MR signals, a patient table on which the object 18 is placed, and a patient table moving system for moving the table in the body axis direction (e.g., z-axis direction) of the object. The MRI system can also include one or more computing devices such as the example computing device of FIG. 1B. A computing device can be operably coupled to the MRI system, for example, using by any medium that facilitates data exchange between the MRI system and the computing device including, but not limited to, wired, wireless and optical links. For example, a computing device can be configured to convert the MR signals received by the transmitting and receiving unit 16 into k-space data. A computing device can also be configured to generate MR image data from the k-space data by image reconstruction processing. Further, the MRI system can optionally include a workflow setting unit, an imaging operation determining unit, a display unit, an input unit, and a controller system.

The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by the input unit is minimized, an imaging time of each imaging method in the shortest performing order, and the like. The imaging operation determining unit determines whether an imaging operation during a main imaging according to the workflow. This disclosure contemplates that the workflow setting unit and/or the imaging operation unit can be implemented using hardware, software, and or a combination thereof. The display unit displays image data such as local image data, diagnosis image data using display, printer and other displayer. The input unit is manipulated by an operator to input signals to the MRI apparatus to set the imaging method group, the performing order, the imaging condition, and the like. The controller system is composed of a processor and integrally controls the respective units of the MRI system described above.

The static magnetic field generating unit 12 includes a main magnet to generate a strong static magnetic field in proximity to the object. The gradient magnetic field generating unit 14 includes gradient magnetic field coils for generating gradient magnetic fields in an x-axis direction, a y-axis direction, and a z-axis direction, which are orthogonal to each other. The transmitting and receiving unit 16 includes a transmission coil and a transmitter unit for irradiating the RF pulses to the object and a receiving coil and a receiver unit for receiving MR signals generated by the object. Optionally, a transceiver coil having the functions of both the transmission coil and the receiving coil can be used. The receiving coil may be composed of, for example, a so-called array coil in which, for example, a plurality of coil elements are disposed to detect the MR signals generated by the object.

The image reconstruction unit includes an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Example Computing Device

It should be appreciated that the logical operations described herein with respect to the various figures may be implemented (1) as a sequence of computer implemented acts or program modules (i.e., software) running on a computing device (e.g., the computing device described in FIG. 1B), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 1B:
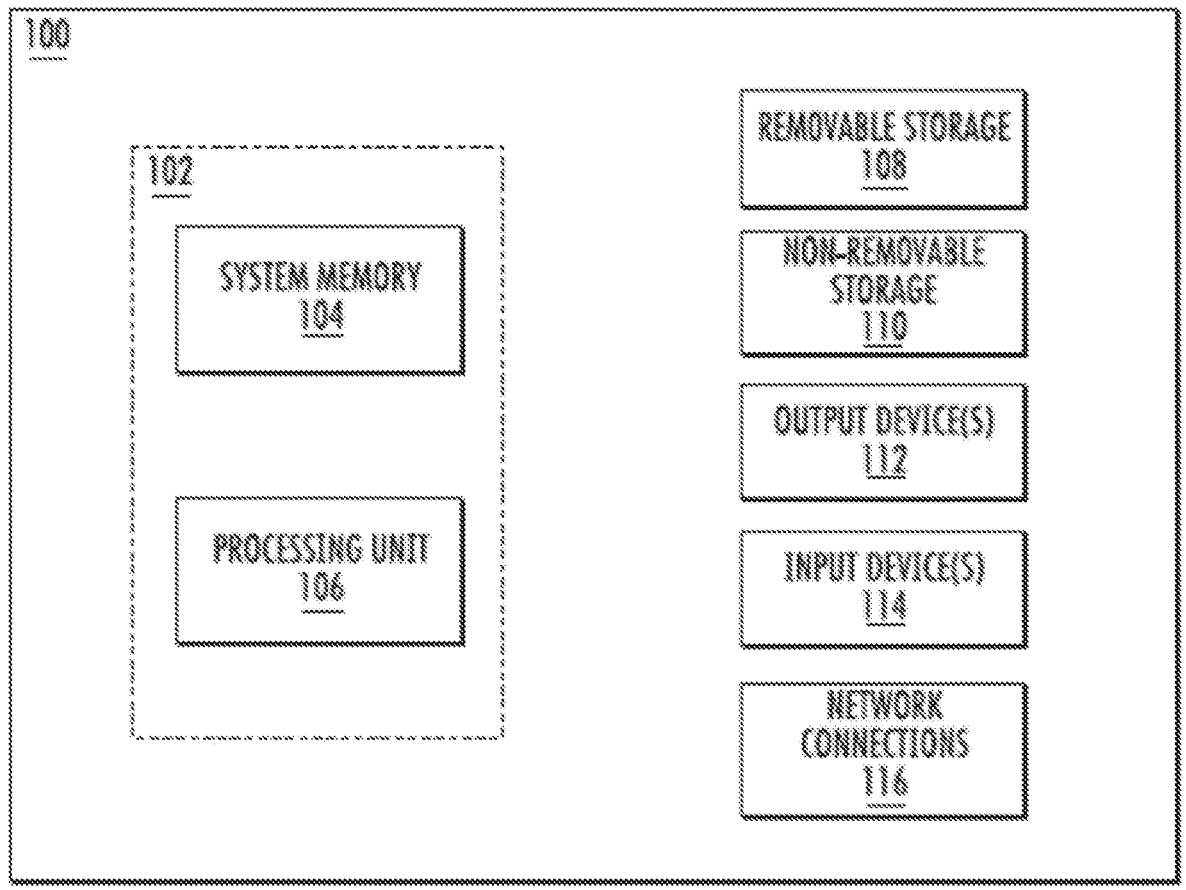
FIG. 1B is an example computing device.

Referring to FIG. 1B, an example computing device 100 upon which embodiments of the invention may be implemented is illustrated. It should be understood that the example computing device 100 is only one example of a suitable computing environment upon which embodiments of the invention may be implemented. Optionally, the computing device 100 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 100 typically includes at least one processing unit 106 and system memory 104. Depending on the exact configuration and type of computing device, system memory 104 may be volatile (such as random access memory (RAM)), non-volatile (such as read-only memory (ROM), flash memory, etc.), or some combination of the two. This most basic configuration is illustrated in FIG. 1B by dashed line 102. The processing unit 106 may be a standard programmable processor that performs arithmetic and logic operations necessary for operation of the computing device 100. The computing device 100 may also include a bus or other communication mechanism for communicating information among various components of the computing device 100.

Computing device 100 may have additional features/functionality. For example, computing device 100 may include additional storage such as removable storage 108 and non-removable storage 110 including, but not limited to, magnetic or optical disks or tapes. Computing device 100 may also contain network connection(s) 116 that allow the device to communicate with other devices. Computing device 100 may also have input device(s) 114 such as a keyboard, mouse, touch screen, etc. Output device(s) 112 such as a display, speakers, printer, etc. may also be included. The additional devices may be connected to the bus in order to facilitate communication of data among the components of the computing device 100. All these devices are well known in the art and need not be discussed at length here.

The processing unit 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the processing unit 106 for execution. Example tangible, computer-readable media may include, but is not limited to, volatile media, non-volatile media, removable media and non-removable media implemented in any method or technology for storage of information such as computer readable instructions, data structures, program modules or other data. System memory 104, removable storage 108, and non-removable storage 110 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 106 may execute program code stored in the system memory 104. For example, the bus may carry data to the system memory 104, from which the processing unit 106 receives and executes instructions. The data received by the system memory 104 may optionally be stored on the removable storage 108 or the non-removable storage 110 before or after execution by the processing unit 106.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Imaging

In order to obtain a detectable nuclear magnetic resonance (NMR) or magnetic resonance imaging (MRI) or magnetic resonance (MR) signal, the object being imaged (also referred to herein as "object" or "subject") must be exposed to a static basic magnetic field (usually designated as the $B_0$ field) which is as homogeneous as possible. The basic magnetic field can be generated by a basic field magnet of the MRI system. While the magnetic resonance images are being recorded, the basic magnetic field has fast-switched gradient fields superimposed on it for spatial encoding, which are generated by gradient coils. Moreover, using radio-frequency (RF) antennas, radio-frequency pulses with a defined field strength are radiated into the objected being imaged. Using these RF pulses, the nuclear spins of the atoms in the object being imaged are excited such that the atoms are deflected by a so-called "excitation flip angle" (α) from their equilibrium position parallel to the basic magnetic field $B_0$. The nuclear spins then process around the direction of the basic magnetic field $B_0$. The magnetic resonance signals generated in this manner are recorded by RF receiver coil. The receiver coil can be either the same coil which was used to generate the RF pulses (i.e., a transceiver coil) or a separate receive-only coil.

The magnetic resonance images of the object are generated based on the received magnetic resonance signals. The MR signal is picked up by a receive coil, amplified and processed. The acquired measurements are digitized and stored as complex numerical values in a "k-space" matrix.

An associated MR image can be reconstructed from the k-space data, for example, by an inverse 2D or 3D fast Fourier transform (FFT) from raw data, which are collected in the spatial frequency domain (the "k-space"). The k-space data includes multiple lines acquired with different phase encoding. Each line is digitized by collecting a number of samples. A set of k-space data is converted to a MR image by means of Fourier transformation. Each image point in the magnetic resonance image is assigned to a small body volume known as a "voxel" and each brightness or intensity value of the images points is linked to the signal amplitude of the magnetic resonance signal received from this voxel. The relationship between the resonantly radiated $B_1^+$ and the flip angle $\alpha(x)$ is assumed by the following equation:

$$\alpha(x)=2\pi\gamma B_1^+(x)\int_0^T f(t)dt$$

where $\gamma$ is the gyromagnetic ratio, which can be considered to be a fixed material constant for most nuclear spin studies, and $\tau$ is the influence duration of the radio-frequency pulse. f(t) is the time dependent transmitter voltage defining the RF pulse shape. The equation above holds true if the frequency of the RF pulse equals the Larmor-frequency of the magnetization.

Before the commencement of each NMR or MRI scan, it is common practice to adjust the strength of the transmit field and/or the receiver sensitivity to ensure that the RF excitation pulses have the optimal frequency, strength and duration to evoke the desired NMR or MRI or MR signal. This does not necessarily mean that the expected RF transmit field will be produced uniformly throughout a cross section and/or a volume of the object being imaged, or that the resulting NMR or MRI or MR signals will be received uniformly from all locations. Transmit RF field produced by most transmit coils as loaded by the object being imaged is not homogeneous, and the receive field of most receive coils is similarly not homogeneous. This is particularly true of imperfect coil configuration, such as surface coil and phase array coils. Even if the transmit and receive coil fields are homogeneous for free space (i.e., the unloaded space or space in the absence of the object), wave behavior and penetration of the RF field into the subject may give rise to non-uniform transmit field and receiver sensitivity throughout the region of interest. This is known as the subject loading effect, and this effect becomes pronounced at higher static $B_0$ magnetic fields such as at static magnetic field of about 3 Tesla or higher. Even at lower static magnetic fields, the subject loading effect may be non-negligible. Moreover, the incorrect calibration of the RF pulse amplitude, instability or drift of the RF amplifier or other RF electronics, can lead to non-uniform transmit field. Also, mutual inductance between the transmit and receive coils may cause further inhomogeneities in the transmit and receive fields.

Theory

Various factors, such as transmit coil configuration, uncompensated eddy currents, wave behavior and object positioning, generate inhomogeneous transmit field. The nominal flip angle of $\alpha$ is defined by averaged flip angles cross volume being imaged. Thus, the actual flip angle should be a function of location. The goal of $B_1^+$ mapping is to estimate the function of flip angle as a space distribution. In most MRI applications, only magnitude images are used. However, phase information is very fundamental, if not more fundamental than magnitude, considering the fact that MR signal magnitude changes are often ultimately due to spin "de-phasing". In k-space, phase of the raw data has been demonstrated to carry more information than magnitude for visualization.

The MR image phase is given:

$$\phi_{image}=\Sigma_i^N\phi_{Ti}+\phi_{B0}+\phi_{Rec}\phi_{syn} \quad (1)$$

Where $\phi_{Ti}$ is the phase of the $B_{1,t}^+$ field for the $i^{th}$ RF pulse. This phase $\phi_{syn}$ is a constant, and therefore assumed to be zero. $\phi_{B0}$ is the phase accumulation of phases which result from at least one of $B_0$ inhomogeneity, flow, eddy current, and chemical shift. The receive phase, $\phi_{Rec}$, is a phase of the receive coil which is spatial function at the high field strength. $\phi_{syn}$ is a reference phase which is the sum of reference phases from transmitter radiofrequency synthesizer, receiver radiofrequency synthesizer, and digitizer. Thus, estimating the phase of $B_1^+$ is very important and useful in MRI.

For the first image, $$\phi_{image,1}=\Phi_\alpha+\phi_{B0}+\phi_{Rec}+\phi_{syn} \quad (2)$$

For the second image, $$\phi_{image,2}=\Phi_\alpha+\Phi_\beta+\phi_{B0}+\phi_{Rec}+\phi_{syn} \quad (3)$$

From Eqns. (2) and (3)

$$\Phi_\beta=\phi_{image,2}-\phi_{image,2} \quad (4)$$

To minimize the effect of $B_0$ inhomogeneity, some sequences, such as spin echo, steady state free precession, ultra-short echo time, and zero echo time sequences, are used to simplify the Eqn. (1) as:

$$\phi_{image}=\Sigma_i^N\phi_{Ti}+\phi_{Rec}\phi_{syn} \quad (5)$$

Methods and Results

Figure 2A:
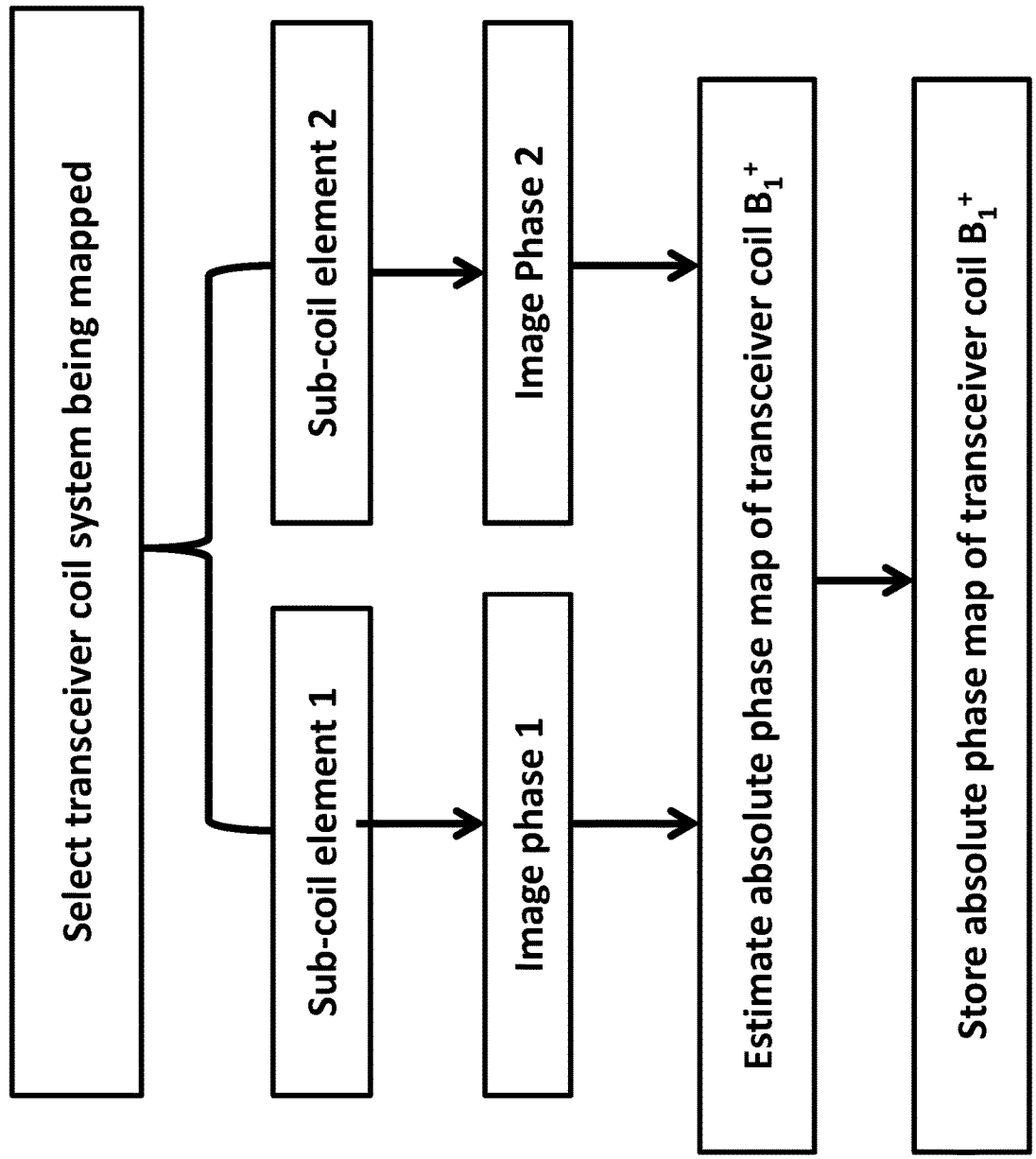
FIG. 2A is a flowchart illustrating example operations for estimating absolute phase mapping of transceiver coil $B_1^+$ according to an implementation described herein.

Referring now to FIG. 2A, example operations for estimating absolute phase of $B_{1,t}^+$ maps for a transceiver according to one implementation is provided. FIG. 2A is a schematic flowchart of estimating absolute phase mapping of transceiver coil $B_{1,t}^+$ in image domain. The estimation of absolute phase mapping of transceiver coil $B_{1,t}^+$ can include the following steps: (a) selecting a transmit coil for which to measure the absolute phase of the RF transmit field $B_1^+$; and (b) exciting nuclear spins in magnetic resonance (MR) nuclei using at least two transmit coil configurations of the transmit coil. For example, quadrature-driven birdcage transceiver coil is equal to the combination (subtraction) of linear-driven (e.g., sub-coil element 1 in FIG. 2A) and anti-quadrature-driven (sub coil-element 2 in in FIG. 2A) birdcage coils. Additionally, a transmit surface coil can be equal to the subtraction of combined transmit coil and another transmit coil. Another coil should be decoupled with the surface coil. The combined coil comprises of both the surface coil and the decoupled coil. The example operations can also include (c) detecting first MR signals and second MR signals arising from exciting nuclear spins in MR nuclei using a first transmit coil configuration and a second transmit coil configuration, respectively. For example, nuclear spins can be excited in magnetic resonance (MR) nuclei using birdcage coil with both linear-driven phase and anti-quadrature-driven phase so that the absolute phase of birdcage coil with quadrature-driven phase could be estimated. The example operations can also include (d) acquiring a first set of complex k-space data and a second set of complex k-space data from the first MR signals and the second MR signals, respectively. This disclosure contemplates that at least these two complex images can be acquired for estimating the absolute phase of the transmit coil. The example operations can also include (e) transforming the first set of complex k-space data and the second set of complex k-space data into a first image and a second image, respectively, and (f) estimating an absolute phase $B_1^+$ map of the transmit coil using the first image and the second image. For example, the absolute phase of quadrature driven birdcage coil can be estimated by the subtraction of phase images acquired using birdcage coil with both linear-driven phase and reverse-quadrature-driven phase. Because the images with linear-driven and reverse-quadrature-driven birdcage coils are acquired with identical imaging parameters, the phase subtraction removes the effect of $B_0$ inhomogeneity, eddy current, chemical shift and absolute receive phase on the estimated absolute phase of the quadrature-driven birdcage transceiver coil. Moreover, the estimation of absolute phase for the transmit coil needs more than two complex images. The number of images are dependent on the elements of the transmit coil being estimated and the combination type of each elements. Additional examples are discussed in further detail below.

Figure 2B:
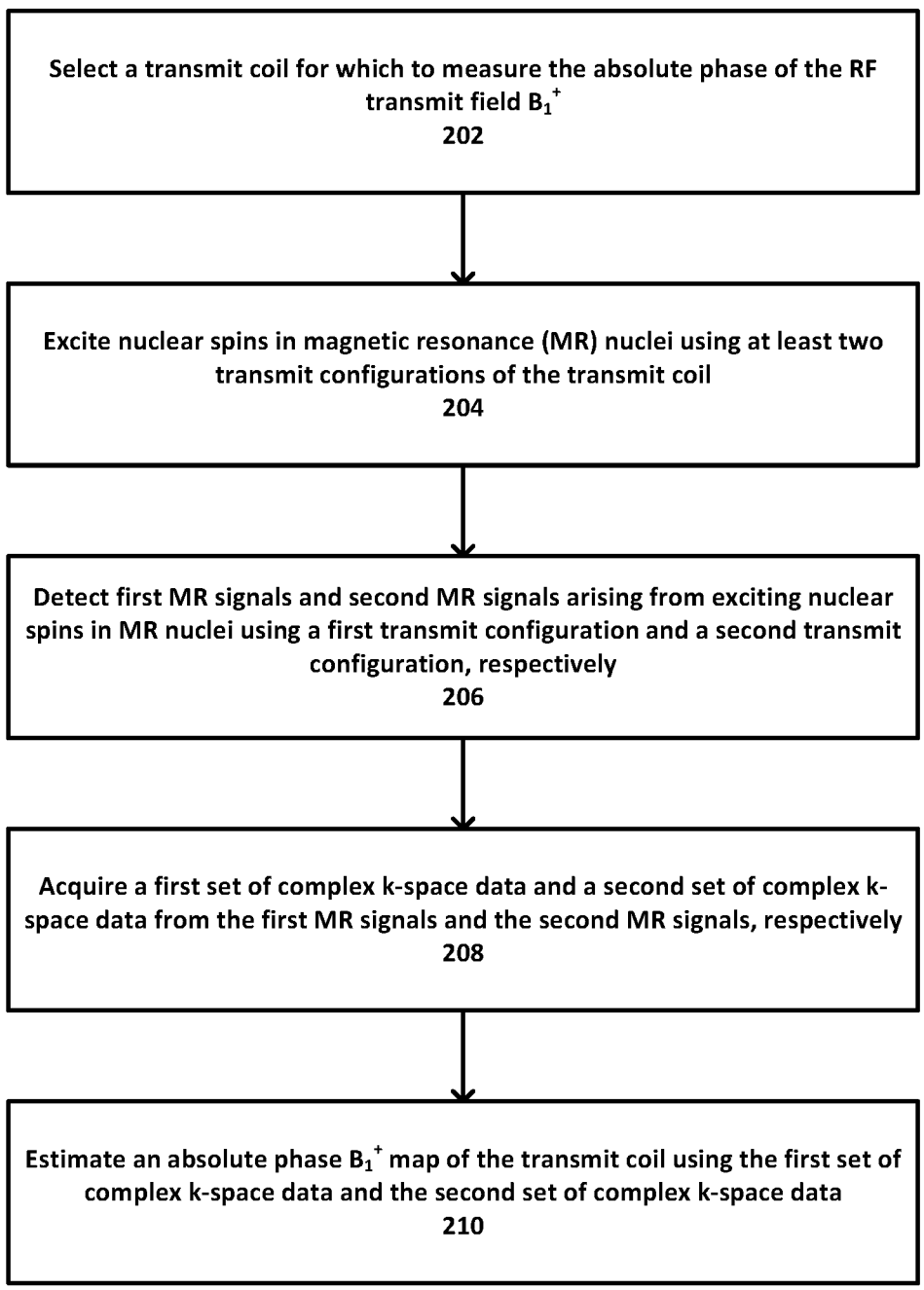
FIG. 2B is another flowchart illustrating example operations for determining spatial distribution of an absolute phase of RF transmit field $B_1^+$ in an MRI system according to an implementation described herein.

Referring now to FIG. 2B, a flowchart illustrating example operations for determining spatial distribution of an absolute phase of RF transmit field $B_1^+$ in an MRI system is shown. This disclosure contemplates that the operations can be performed using the MRI system and/or computing device described with regard to FIGS. 1A and 1B. At 202, a transmit coil for which to measure the absolute phase of the RF transmit field $B_1^+$ can be selected. For example, the transmit coil can be a transceiver birdcage coil (e.g., transceiver birdcage coil of FIGS. 3A-3F below). It should be understood that this is provided only as one example and the transmit coil can be a different type of coil. At 204, nuclear spins can be excited in magnetic resonance (MR) nuclei using at least two transmit configurations of the transmit coil (e.g., sub-coil element 1, sub-coil element 2, etc.). For example, a first transmit configuration can be the linear mode of a transceiver birdcage coil, and a second transmit configuration can be the reverse quadrature mode of a transceiver birdcage coil. At 206, first MR signals and second MR signals arising from exciting nuclear spins in MR nuclei using a first transmit configuration and a second transmit configuration, respectively, can be detected. At 208, a first set of complex k-space data and a second set of complex k-space data can be acquired from the first MR signals and the second MR signals, respectively. At 210, an absolute phase $B_1^+$ map of the transmit coil can be estimated using the first set of complex k-space data and the second set of complex k-space data.

Optionally, the first set of complex k-space data and the second set of complex k-space data (e.g., obtained in Step 208 above) can be transformed into a first image and a second image, respectively. As described herein, an MR image can be reconstructed from the k-space data, for example, by an inverse 2D or 3D fast Fourier transform (FFT) from raw data, which are collected in the spatial frequency domain (the "k-space"). Using the linear and reverse quadrature modes of the transceiver birdcage coil, the resulting first and second images are those of FIGS. 3A and 3C, for example. The absolute phase $B_1^+$ map of the transmit coil can be estimated using the first and second images. For example, the absolute phase $B_1^+$ map of the transceiver birdcage coil with quadrature mode (e.g., shown in FIG. 3E) can be obtained by subtracting the first image (e.g., phase image with linear mode of FIG. 3A) and the second image (e.g., phase image with reverse quadrature mode of FIG. 3C).

Figure 3C:
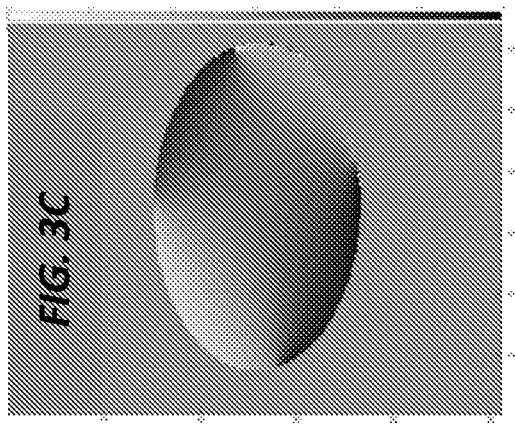
FIGS. 3A-3F illustrate estimation of absolute phase of $B_{1,t}^+$ of a transceiver birdcage coil with a spherical phantom. The phase images shown in FIGS. 3A-3C are acquired with linear driven phase (FIG. 3A), quadrature driven phase (FIG. 3B), and reverse quadrature driven phase (FIG. 3C) at identical imaging parameters, respectively. The birdcage coil with linear driven phase comprises the coil channels 1 and 2 with the same phase. The birdcage coil with quadrature driven phase comprises the coil channel 1 with 0 degree phase and the coil channel 2 with 90 degree phase to generate a positive circularly polarized RF field. The birdcage coil with reverse quadrature driven phase comprises the coil channel 1 with 90 degree phase and the coil channel 2 with 0 degree phase to generate a negative circularly polarized RF field.
Figure 3F:
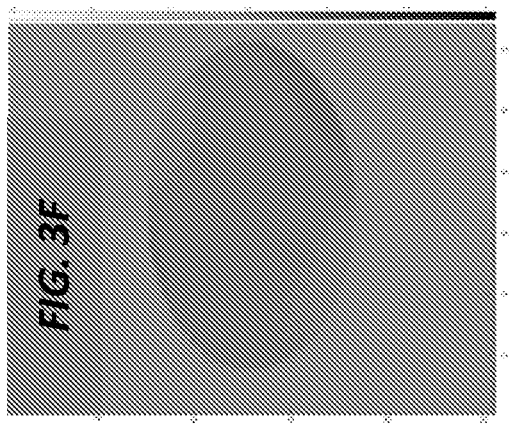
Figure 3B:
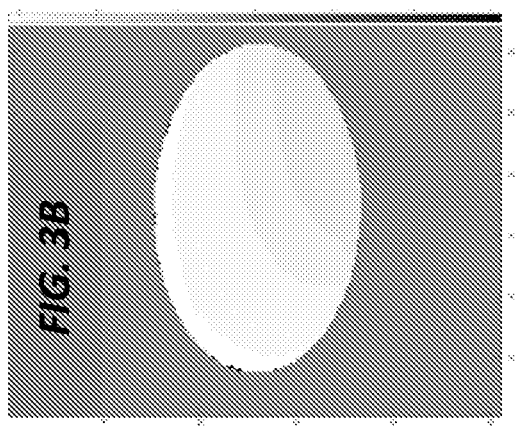
Figure 3E:
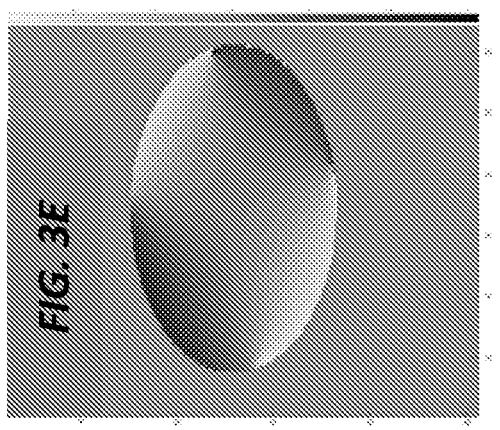
Figure 3A:
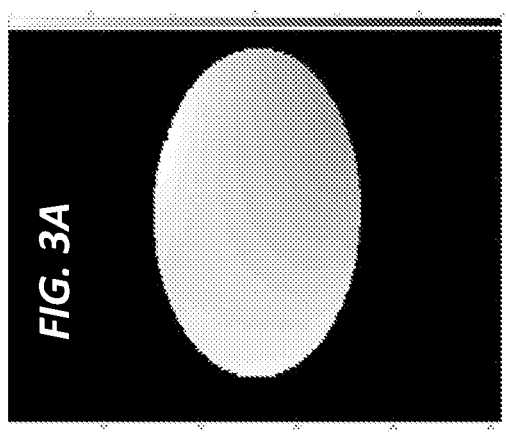
Figure 3D:
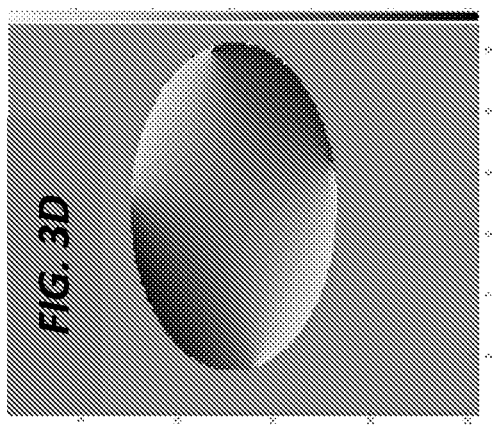

FIGS. 3A-3F illustrate estimation of absolute phase of $B_{1,t}^+$ of a transceiver birdcage coil with a spherical phantom. The transmit birdcage coil with the different phase combination can create three sub-coil configurations: (i) linear mode in which channel 1 and channel 2 of birdcage coil have an identical phase; (ii) quadrature mode in which phase of channel 1 has a 90 degree phase shift with phase of channel 2 to generate positive circularly polarized radiofrequency field [Wang J et al., Polarization of the RF field in a human head at high field: a study with a quadrature surface coil at 7.0 T, Magn Reson Med. 2002; 48:362-369]; (iii) reverse quadrature mode in which phase of channel 1 has a 90 degree phase shift with phase of channel 2 to generate negative circularly polarized radiofrequency field [Wang J et al., Polarization of the RF field in a human head at high field: a study with a quadrature surface coil at 7.0 T, Magn Reson Med. 2002; 48:362-369]. These sub-coil configuration are examples of "transmit configurations" or "transmit coil configurations" described herein. In order to simplify the calculation, the phase for linear mode is selected for 90 degree, the phase for quadrature mode is selected for channel 1 of 0 degree and channel 2 of 90 degree, and the phase for reverse quadrature mode is selected for channel 1 of 90 degree and channel 2 of 0 degree. In FIGS. 3A-3C, three phase images were acquired with linear mode (FIG. 3A), quadrature mode (FIG. 3B), and reverse quadrature mode (FIG. 3C), respectively. All the images were acquired with identical receive coil configuration and image parameters which generate identical phase shifts caused by factors including, but not limited to, $B_0$ inhomogeneity, chemical shift, eddy current, flow. According to these phase images, the absolute phase image of a birdcage transmit coil with quadrature mode is equal to the subtraction of the phase image with linear mode (FIG. 3A) and the phase image with reverse quadrature mode (FIG. 3C), which is shown in FIG. 3E. Similarly, the absolute phase image of a birdcage transmit coil with reverse quadrature mode is equal to the subtraction of the phase image with linear mode (FIG. 3A) and the phase image with quadrature mode (FIG. 3B), which is shown in FIG. 3F. The absolute phase image of a birdcage transmit coil with linear mode is equal to the addition of the absolute phase image with quadrature mode (FIG. 3E) and reverse quadrature mode (FIG. 3F), which is shown in FIG. 3D.

Figure 4:
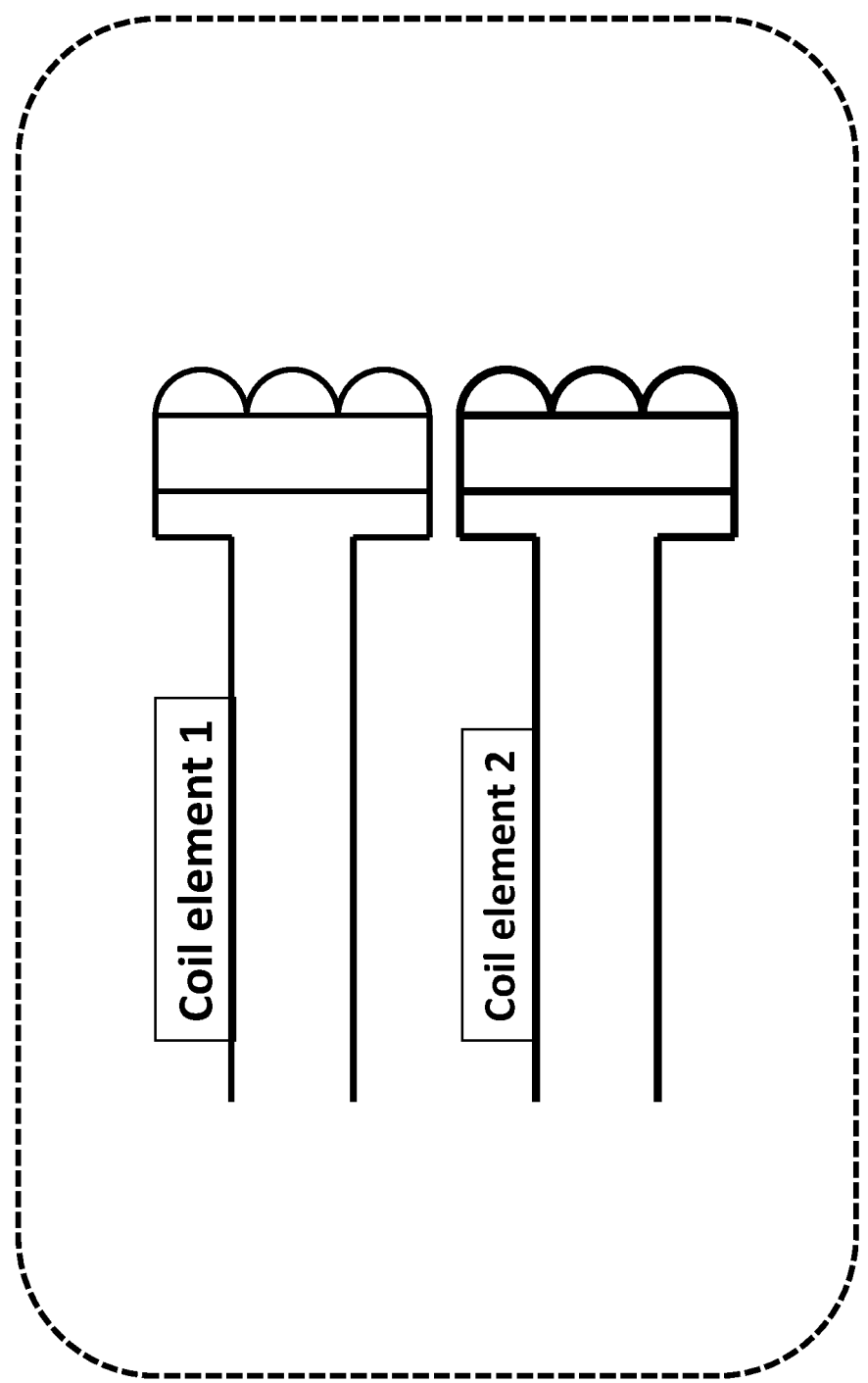
FIG. 4 is a diagram illustrating a dual transmit coil configuration for estimating $B_{1,t}^+$ absolute phase mapping of a transmit coils according to an implementation described herein. The dual transmit coil comprises of coil element 1 and coil element 2. Ideally, coil element 1 and coil element 2 are assumed to be independent. That is, it is possible to assume the coupling between coil elements 1 and 2 is negligible.
Figures 7A, 7B, 7C, 7D:
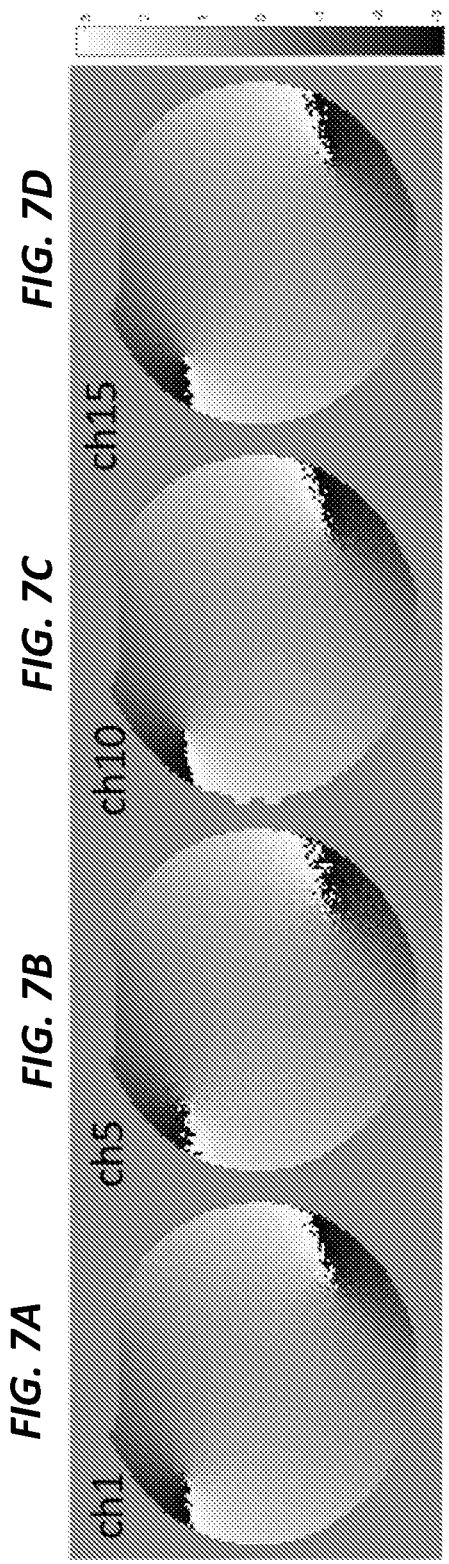
FIGS. 7A-7D illustrate estimation of absolute phase of $B_{1,t}^+$ of dual transmit coils with a spherical phantom.

An example method for determining a spatial distribution of an absolute phase of a radio frequency (RF) dual transmit field $B_{1,t}^+$ in a magnetic resonance imaging (MRI) system is described below. The method can include acquiring data using two coil configurations or coil elements, such as configuration in FIG. 4. Each coil element can be comprised of at least one of surface coil, volume coil, element of coil array. For example, as described above, nuclear spins can be excited using each of the coil configurations such that respective sets of complex k-space data are obtained (i.e., a complex set of k-space data associated with each of the coil configurations). The sets of complex k-space data can then be transformed into respective images (e.g., by Fourier transform). Additionally, the transmit coil being measured can be combined with the two transmit coil elements by either subtraction or addition. For example, as described herein, phase images associated with the different coil configurations can be combined and/or subtracted to obtain the absolute phase of the RF transmit field $B_{1,t}^+$. Ideally, coil element 1 and coil element 2 are assumed to be independent. That is, the coupling between coil 1 and 2 is negligible. If the number of transmit coil elements is greater than two, the elements can be separated into the combination of various dual transmit coil. In this case, the techniques described herein can be extended for any multiple transmit coil.

Alternatively or additionally the different transmit coil configurations can include, but are not limited to, an array of transmit coil elements and a quadrature transmit volume coil. This disclosure contemplates that if the transmit coil which absolute phase will be measured is the addition of the two transmit coil configuration, three images should be acquired with identical image parameters using the two transmit coil configuration and their addition combination. Alternatively, if the transmit coil which absolute phase will be measured is the subtraction of the two transmit coil configuration, two images should be acquired with identical image parameters using the two transmit coil configuration.

Optionally, the coupling between coil elements influence the result of the measured absolute phase.

Optionally, the estimated absolute phase map of transmit coil $B_{1,t}^+$ in the k-space domain of at least a portion of a transmit coil of the MRI system can be obtained by estimating a k-space domain convolution kernel between k-space of the at least two complex images. For example, the k-space domain convolution kernel can optionally be estimated using a fitting algorithm such as a least-square algorithm. It should be understood that the least-square algorithm is provided only as an example and that other fitting algorithms may be used.

Alternatively or additionally, the two phase images can be acquired using at least two different MRI system configurations. For example, the two MRI system configurations include, but are not limited to, different two coil elements of a transmit coil, transmit elements with different phase combination.

Alternatively or additionally, the phase images can be acquired with any fast image techniques. For example, partial Fourier acquisition, echo train [Mugler J P, J Magn Reson Imaging. 2014; 39:745-67] and k-space under-sampling [Jaspan O N, et al., Br J Radiol. 2015; 88:1056] can be applied to reduce the time for estimating absolute phase of transmit coils and receive coils.

Alternatively or additionally, the phase images can be combined with any k-space trajectories including, but not limited to, Cartesian, spiral, radial, Zig_zag.

Alternatively or additionally, the phase images for sub-coil or sub-coil group or coil element can be acquired using identical imaging parameters. For example, the imaging parameters can include, but are not limited to, resolution, geometric location, repetition time (TR), echo time (TE), flip angle, inversion recovery time, and/or receiver bandwidth.

FIGS. 5A-5D illustrate estimation of absolute phase of $B_{1,t}^+$ of dual transmit coils with a spherical phantom using phase images acquired with both each individual coil and their combination. The individual coils and their combination are examples of "transmit configurations" or "transmit coil configurations" described herein. For example, the dual transmit coils can be formed by two volume coils. The receive coil can be a 16 channel head coil array. The combined dual transmit coil can be driven with quadrature phase (i.e., coil element 1 with phase of 0 degree and coil element 2 with phase of 90 degree). The absolute phase of coil element 1 with phase of 0 degree is equal to the subtraction of two phase images acquired using the dual transmit coil with the phase 0 degree and coil element 2 with phase of 0 degree. The absolute phase of coil element 2 with phase of 90 degree is equal to the subtraction of two phase images acquired using the dual transmit coil with the phase 90 degree and coil element 1 with phase of 90 degree. Generally, the difference in the phase images acquired using the dual transmit coil with the phase of 0 and 90 degree is equal to 90 degree. Thus, only of the phase images acquired using the dual transmit coil with the phase of 0 and 90 degree should be acquired to save the time. The absolute phase for dual transmit coil with quadrature phase is the addition of the absolute phases of coil element 1 with phase of 0 degree and coil element 2 with phase of 90 degree. The absolute phase images in FIGS. 5A-5D correspond to the channels 1, 5, 10, and 15 of the 20-channel head coil, respectively. In FIGS. 5A-5D, all absolute phases for dual transmit coil with quadrature phase estimated from each individual receive channel are in agreement. This indicates that the absolute phase of transmit coil is independent of receive coil type.

Similarly, absolute phase of $B_{1,t}^+$ of dual quadrature driven transmit coils with a volunteer brain (e.g., in vivo tissue) can be estimated using method described in FIGS. 5A-5D. The results are shown in the images of FIGS. 6A-6D which are corresponding to the different axial slices of the brain.

Similarly to the transceiver birdcage coil described with respect to FIGS. 3A-3F, absolute phase of $B_{1,t}^+$ of dual quadrature driven transmit coils with a spherical phantom is comprised by the dual coil with the linear driven phase and reverse quadrature driven phase. The dual transmit coil is driven with quadrature phase (i.e., coil element 1 with phase of 0 degree and coil element 2 with phase of 90 degree). The absolute phase of quadrature-driven dual transmit coil is equal to the subtraction of two phase images acquired with dual transmit coil with linear driven phase and reverse quadrature driven phase, which is shown by the images in FIGS. 7A-7D. The absolute phase images in FIGS. 7A-7D correspond to the channels 1, 5, 10, and 15 of the 20-channel head coil, respectively. In FIGS. 7A-7D, all absolute phases for dual transmit coil with quadrature phase estimated from each individual receive channel are in agreement. This indicates that the absolute phase of transmit coil is independent of receive coil type.

Similarly, an absolute phase of $B_{1,t}^+$ of dual transmit coils with a volunteer brain (e.g., in vivo tissue) is estimated using method described in FIGS. 7A-7D. The results are shown in the images of FIGS. 8A-8D which are corresponding to different axial slices of the brain.

Alternatively or additionally, the methods described herein for estimating absolute phase map of $B_{1,t}^+$ can be available for any receive coil, including at least one of surface coil, volume coil, array coil.

Alternatively or additionally, the phase images for estimating absolute phase map of $B_{1,t}^+$ can be acquired with each of the transmit coil configurations using identical imaging parameters when exciting nuclear spins in MR nuclei.

Alternatively or additionally, the phase images for estimating absolute phase map of $B_{1,t}^+$ can be acquired first in k-space and then transformed from k-space to image domain. As described herein, an MR image can be reconstructed from the k-space data, for example, by an inverse 2D or 3D fast Fourier transform (FFT) from raw data, which are collected in the spatial frequency domain (the "k-space").

Another example method for determining a spatial distribution of the absolute phase map of radio frequency (RF) transmit field $B_{1,t}^+$ in a magnetic resonance imaging (MRI) system is described herein. The method can include acquiring at least two complex images in a k-space domain from MR nuclei within an imaged volume, transforming the at least two complex images into an image domain, estimating a complex $B_{1,t}^+$ map in the image domain of at least a portion of a transmit coil of the MRI system, and storing the complex $B_{1,t}^+$ map in a memory.

Alternatively or additionally, the MRI system includes a plurality of RF transmit channels or elements. The method can optionally include, using the absolute phase map of $B_{1,t}^+$ map of each of the RF transmit channels or elements, performing RF shimming or tailored RF shimming.

Alternatively or additionally, the method can optionally include, using the absolute phase map of $B_{1,t}^+$, improving the precision of quantitative MRI [Wang et al., J Magn Reson. 2006; 182(2):283-92]. For example, the quantitative MRI can include, but is not limited to, $T_1$ mapping, $T_2$ imaging, water/fat fraction, molecule concentration for magnetic resonance spectroscopy (MRS), and/or magnetic resonance spectroscopy imaging (MRSI).

Alternatively or additionally, the method can optionally include, using the absolute phase map $B_{1,t}^+$, estimating an absolute phase map $B_{1,r}^-$ map.

Alternatively or additionally, the method can optionally include, using the absolute phase map $B_{1,t}^+$, improving performance of simultaneous multi-slice imaging techniques [Feinberg D A, Setsompop K. J, Magn Reson. 2013; 229: 90-100].

Alternatively or additionally, the method can optionally include, using the absolute phase map of $B_{1,t}^+$, determining local specific absorption rate (SAR), which is a measure of the rate at which energy is absorbed by the human body when exposed to a radio frequency (RF) electromagnetic field [Katscher et al., Magn Reson Med. 2012; 68:1911-1918].

Figure 9:
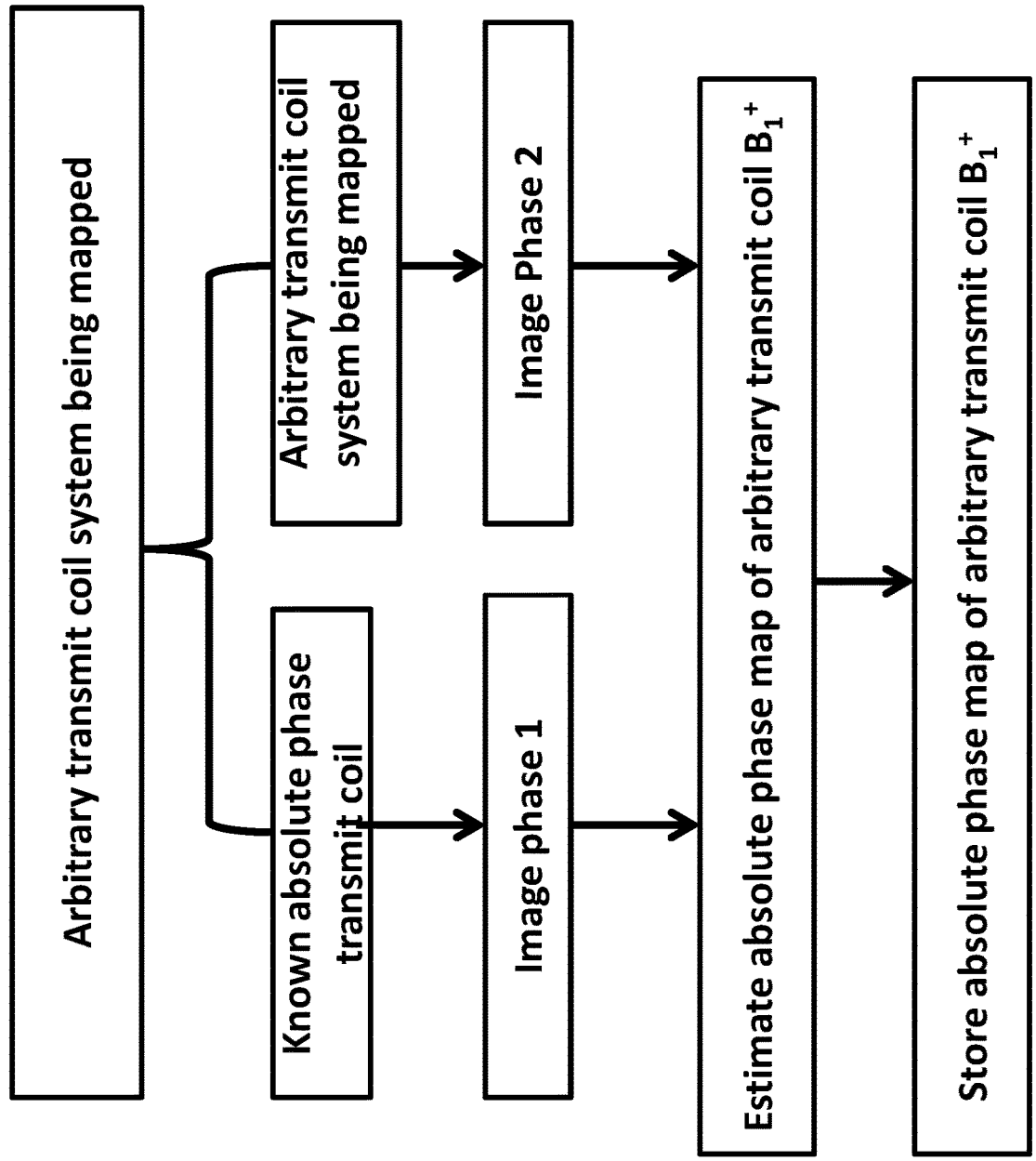
FIG. 9 is a flowchart illustrating example operations for estimating $B_1^+$ absolute phase mapping of an arbitrary coil according to an implementation described herein.

FIG. 9 is a schematic flowchart of estimating $B_{1,t}^+$ absolute phase mapping of an arbitrary coil. The estimation of absolute phase mapping of the arbitrary coil $B_{1,t}^+$ can include the following steps: (a) acquiring a phase image of known absolute phase of a transmit coil. The measured absolute phase of a transmit coil can be estimated using any method, including but not limited to, the methods described herein (e.g., with regard to FIG. 2A or 2B), symmetry assumption [U.S. 2016/0061921 to Katscher], Local Maxwell Tomography technique [U.S. 2016/0054262 to Sodickson et al.], complex phase of a specific image [U.S. 2014/0103925 to Hancu et al.]. The operations can also include: (b) acquiring a phase image with the arbitrary coil at the identical imaging parameters used in step (a); and (c) estimating the absolute phase of the arbitrary coil using the known absolute phase of the transmit coil acquired in step (a) as a reference. That is, the absolute phase of the arbitrary coil equals to the subtraction of the phase difference of two phase images (in both (a) and (b)) and the known absolute phase. The operations can also include (d) storing the absolute phase of the arbitrary coil, for example, in memory of a computing device.

FIGS. 10A-10C illustrate estimation of absolute phase of $B_1^+$ of dual transmit coils as a quadrature transceiver coil with a spherical phantom. FIGS. 10A-10C show absolute phase of $B_1^+$ estimated from phase images acquired with receive channel 1, receive channel 2 and their combination, respectively. In theory, all absolute phase of $B_1^+$ estimated should be identical because the absolute phase of $B_1^+$ is identical for the identical transmit coil configuration and loading. The absolute phase of $B_1^+$ is also independent of receive coil. The absolute phase of $B_1^+$ in FIG. 10A is very close to that in FIG. 10B. Their tiny difference may result from the imperfect balance of the two channels of quadrature receiver [WO1998032221A1 to Wynn S R]. But, the absolute phase of $B_1^+$ in FIG. 10C is significantly different from that in both FIG. 10A and FIG. 10B. In theory, the absolute phase of $B_1^+$ from either FIG. 10A or FIG. 10B is regarded as a ground truth. The significant error or inaccuracy is caused by the combination of images from receive channel 1 and receive channel 2, which is the most popular method in current MRI imaging. The results shown in FIGS. 10A-10C indicate that current image combination methods are problematic for at least phase image reconstruction. Additionally, these results provide a potential method to evaluate and develop image combination method for improving the accuracy of image combination using obtained absolute phase information of $B_1^+$. This disclosure contemplates extending the method for the combination and reconstruction of MR signal and MRS signal from multi-channel or array coils using obtained absolute phase information of both $B_1^+$ and $B_1^-$.

Figure 11A:
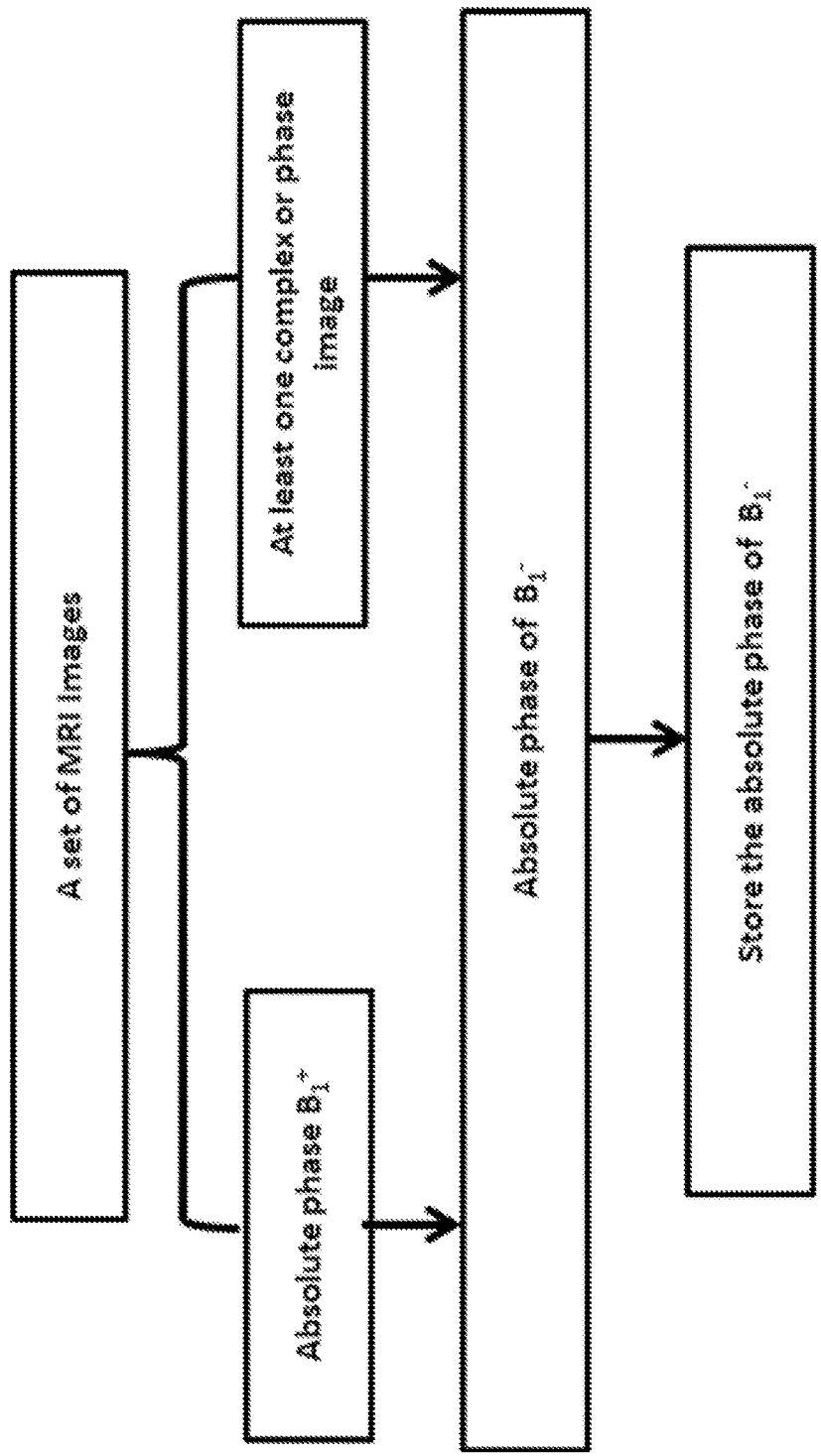
FIG. 11A is a flowchart illustrating example operations for estimating $B_1^-$ absolute phase mapping of any receive coil or coil array according to an implementation described herein.

FIG. 11A is a flowchart illustrating example operations for estimating $B_{1,r}^-$ absolute phase mapping of any arbitrary receive coil or coil array. The estimation of $B_{1,r}^-$ absolute phase mapping can include the following steps: (a) exciting nuclear spins in magnetic resonance (MR) nuclei using a transmit coil of the MRI system; (b) detecting MR signals arising from exciting nuclear spins in MR nuclei using a receive coil of the MRI system; (c) acquiring a complex image from the MR signals; (d) estimating a phase of the complex image; and (e) receiving an absolute phase $B_1^+$ map of the transmit coil of the MRI system. The measured absolute phase of a transmit coil can be estimated using any method, including but not limited to, the methods described herein (e.g., with regard to FIG. 2A or 2B), symmetry assumption [U.S. 2016/0061921 to Katscher], Local Maxwell Tomography technique [U.S. 2016/0054262 to Sodickson et al.], complex phase of a specific image [U.S. 2014/0103925 to Hancu et al.]. The example operations can also include: (f) estimating an absolute phase of $B_1^-$ field of the receive coil using the absolute phase $B_1^+$ map of the transmit coil of the MRI system and the phase of the complex image (or respective phases of two complex images) according to Eqns. (5) or (1) when $\phi_{syn}$ is assumed to be zero; and (g) storing the absolute phase of $B_1^-$ field of the arbitrary receive coil or coil array.

Alternatively or additionally, in some implementations, the complex image can be the same complex image used for estimating the absolute phase $B_1^+$ map of the transmit coil of the MRI system. In other implementations, the complex image can be a different complex image than that used for estimating the absolute phase $B_1^+$ map of the transmit coil of the MRI system.

Figure 11B:
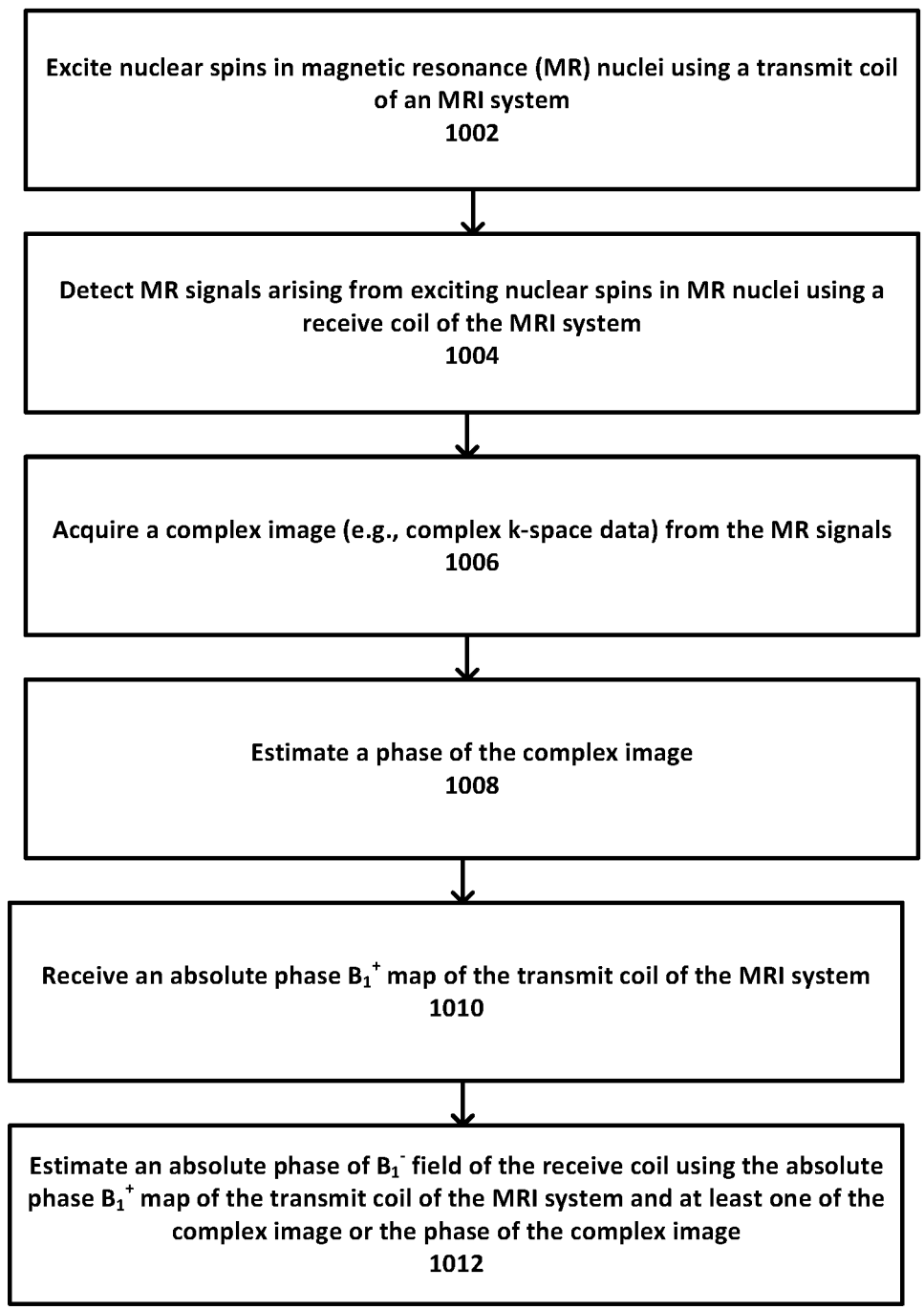
FIG. 11B is another flowchart illustrating example operations for determining spatial distribution of an absolute phase of RF receive field $B_1^-$ in an MRI system according to an implementation described herein.

Referring now to FIG. 11B, a flowchart illustrating example operations for determining spatial distribution of an absolute phase of RF receive field $B_1^-$ in an MRI system is shown. This disclosure contemplates that the operations can be performed using the MRI system and/or computing device described with regard to FIGS. 1A and 1B. At 1002, nuclear spins in magnetic resonance (MR) nuclei can be excited using a transmit coil of the MRI system. At 1004, MR signals arising from exciting nuclear spins in MR nuclei can be detected using a receive coil of the MRI system. At 1006, a complex image (e.g., complex k-space data) can be acquired from the MR signals. At 1008, a phase of the complex image can be estimated. At 1010, an absolute phase $B_1^+$ field of the transmit coil of the MRI system can be received. As discussed herein, this information can be obtained, for example, using the techniques described herein (e.g., as described with respect to FIG. 2A or 2B) or alternatively using any other known technique for estimating absolute phase of the transmit coil. At 1012, an absolute phase of $B_1^-$ field of the receive coil can be estimated using the absolute phase $B_1^+$ field of the transmit coil of the MRI system and at least one of the complex image or the phase of the complex image. For example, as described above, the absolute phase of $B_1^-$ field of the receive coil can be estimated using Eqn. (4).

Alternatively or additionally, the method for estimating the absolute phase map of $B_{1,r}^-$ can be performed using specific sequence to remove minimize the effect of $B_0$ inhomogeneity, such as spin echo, but not limited to, steady state free precession, ultra-short echo time, and zero echo time sequences.

Alternatively or additionally, the method for estimating the absolute phase map of $B_{1,r}^-$ can be performed in either image domain or k-space domain.

FIGS. 12A-12C illustrate a comparison of absolute phases of both $B_1^+$ mapping and $B_1^-$ mapping of a transceiver coil with a spherical phantom. The images are acquired with dual transmit coil as a transmitter and a body coil as a receiver. The phase image in FIG. 12A is acquired with spin echo sequence. The transmit absolute phase image (FIG. 12B) of the transceiver coil can be estimated using method described in FIG. 2A or 2B. The receive absolute phase image of the transceiver coil can be estimated by the subtraction of phase images in FIG. 12A and FIG. 12B according to Eq. (5), which is shown in FIG. 12C. There are significant differences in the estimated absolute phase images in FIG. 12B and FIG. 12C. This indicates that symmetry assumption for estimating the absolute phase introduces a significant error.

Figures 13A, 13B, 13C:
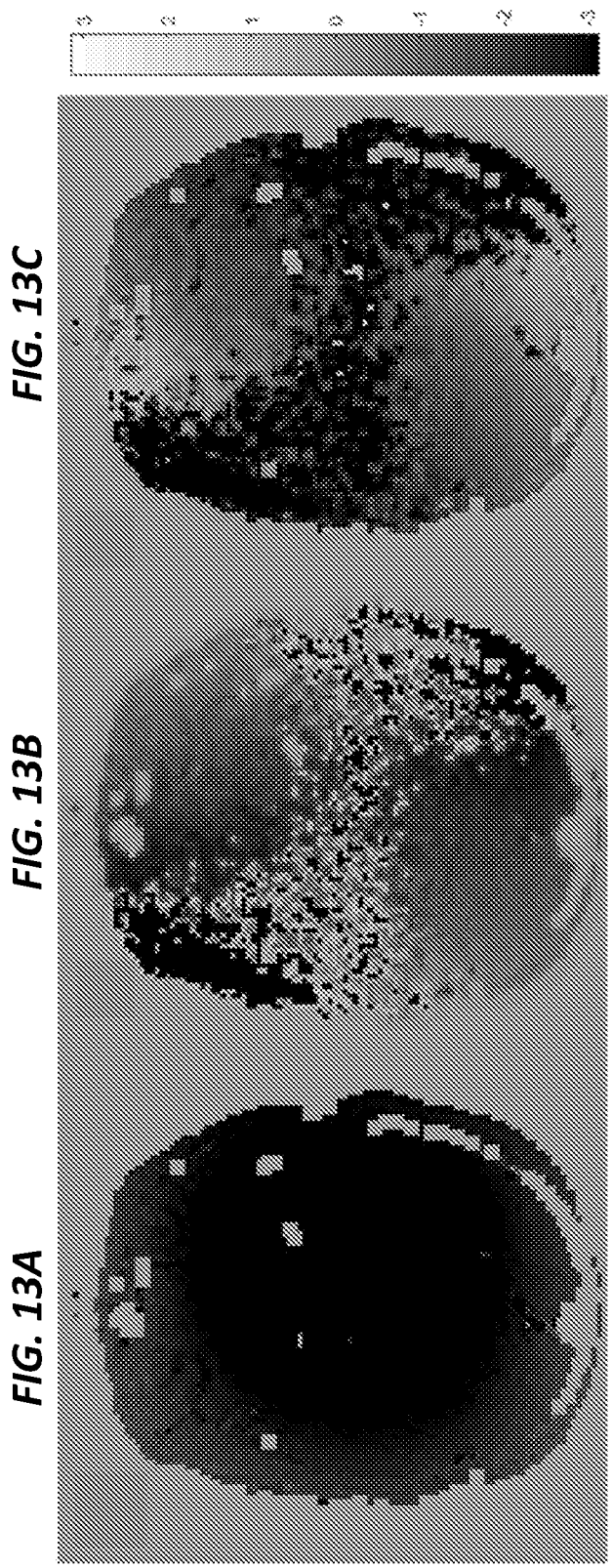
FIGS. 13A-13C illustrate a comparison of absolute phase of $B_{1,t}^+$ mapping and $B_{1,r}^-$ mapping for a transceiver coil with a normal volunteer brain.

FIGS. 13A-13C illustrate a comparison of absolute phases of both $B_{1,t}^+$ mapping and $B_{1,r}^-$ mapping of a transceiver coil with a volunteer brain (e.g., in vivo tissue) is estimated using method described in FIGS. 12A-12C. The images are acquired with dual transmit coil as a transmitter and a body coil as a receiver. The result also indicates that there are significant differences in the estimated absolute phase images in FIG. 13B and FIG. 13C.

FIGS. 14A-14H are the phase images (FIGS. 14A-14D) of a spherical phantom acquired with a quadrature dual transmit coil and absolute receive phases (FIGS. 14E-14H). The images are acquired using spin echo sequence with dual transmit coil as a transmitter and 20 channel head coil as a receiver. The phase images (FIGS. 14A-14D) and absolute receive phases (FIGS. 14E-14H) correspond to receiver channels 1, 5, 10, and 15, respectively, of the 20-channel receive coil. The $B_0$ inhomogeneity caused from inhomogeneity static magnetic field, susceptibility, flow, chemical shift and eddy current can be ignorable. The image phase comprised of transmit phase of the dual transmit coil and receive phase of each individual receive element.

An example method for determining a spatial distribution of the absolute phase map of radio frequency (RF) receiver sensitivity $B_1^-$ in a magnetic resonance imaging (MRI) system is described herein. The method can include acquiring at least two complex images in a k-space domain from MR nuclei within an imaged volume, transforming the at least two complex images into an image domain, estimating the absolute phase map of $B_{1,r}^-$ in the image domain of at least a portion of a receiver coil of the MRI system, and storing the complex $B_{1,r}^-$ map in a memory.

Optionally, the absolute phase map of $B_1^-$ can be estimated using at least one of spin echo, gradient echo, ultra-short echo time, zero echo time, and balanced steady state sequences without $B_0$ information.

Another example method for determining a spatial distribution of an absolute phase of radio frequency (RF) receiver sensitivity $B_1^-$ in a magnetic resonance imaging (MRI) system is described herein. The method can include acquiring at least two phase images in a k-space domain from MR nuclei within an imaged volume, estimating an absolute phase $B_1$: map in the k-space domain of at least a portion of a receiver coil of the MRI system, and storing the complex $B_{1,r}^-$ map in a memory. The two phase images must apply for an absolute phase of $B_1^+$ and then the absolute phase $B_{1,r}^-$ using Eq (4) or Eq. (5).

Optionally, the estimated the absolute phase map of $B_1^-$ in the k-space domain can be obtained by estimating the two phase images of two coil configurations in k-space domain. For example, the k-space domain convolution kernel can optionally be estimated using a fitting algorithm such as a least-square algorithm. It should be understood that the least-square algorithm is provided only as an example and that other fitting algorithms may be used.

Alternatively or additionally, the method can optionally include, using the absolute phase map of $B_1^-$, combining a plurality of images acquired with each of a plurality of coil elements in a coil array of the MRI system.

Alternatively or additionally, the method can optionally include, using the absolute phase map of $B_{1,r}^-$, performing at least one of an MRI image reconstruction algorithm or reducing artifacts in parallel image acquisition [Deshmane A et al., J Magn Reson Imaging, 2012; 36:55-72]. For example, the parallel image acquisition can be performed using at least one of sensitivity encoding (SENSE), PARS, SMASH, or generalized autocalibrating partially parallel acquisitions (GRAPPA) methods [Griswold M A et al., NMR Biomed, 2006 May; 19(3):316-24]. Optionally, parallel image acquisition signals are acquired using a Cartesian or non-Cartesian k-space trajectory.

Alternatively or additionally, the method can optionally include, using the absolute phase map of $B_1^-$, performing quantitative MRI or quantitative magnetic resonance spectroscopy (MRS) with an external reference or an internal reference.

Alternatively or additionally, the method can optionally include, using the an absolute phase map of $B_{1,r}^-$ map, improve the image quality of parallel image acquisition in the MRI system.

Alternatively or additionally, image combination from multi-coil elements or multiple coil array can optionally be derived from an absolute phase map of $B_1^-$ in the MRI system.

The systems and methods described herein: (1) can estimate $B_1^+$ mapping from both image domain and k-space domain; (2) can extend absolute phase $B_1^+$ mapping to any coil configuration which can decompose into the subtraction of two coil configurations. The systems and methods described herein can estimate absolute phase mapping of $B_1^+$ and/or $B_1^-$ from both image domain and k-space domain.

Example Applications

Alternatively or additionally, the absolute phase map of $B_1^+$ and $B_1^-$, can be estimated for a global or regional region of interest (ROI).

Alternatively or additionally, the methods described herein can optionally include, using the absolute phase map of $B_1^+$ and $B_1^-$, performing image compensation to a diagnostic image acquired by the MRI system [Sbrizzi et al, NMR in Biomedicine, 2015; 28(11):1393-401].

Alternatively or additionally, the MRI system includes a plurality of RF transmit channels or elements. The at least two phase images can be acquired using different transmit coil configurations as described herein.

Alternatively or additionally, the methods described herein can optionally include, using the absolute phase map of each of the RF transmit channels or elements, performing RF shimming or tailored RF shimming.

Alternatively or additionally, the methods described herein can optionally include, using the absolute phase map of $B_1^+$ and $B_1^-$, determining a parameter controlling multi-RF transmitter of the MRI system [Padormo et al., NMR in Biomedicine, 2016; 29:1145-1161].

Alternatively or additionally, the methods described herein can optionally include, using the absolute phase map of $B_1^+$ and $B_1^-$, generating a new MRI contrast at different frequencies [Katscher et al., Computational and mathematical methods in medicine, 2013:546562; Zhang et al., IEEE reviews in biomedical engineering, 2014; 7:87-96]. For example, the new MRI contrast can include, but is not limited to, conductivity or permittivity contrast.

Alternatively or additionally, the methods described herein can optionally include, using the absolute phase map of $B_1^+$ and $B_1^-$, determining the electromagnetic property [Katscher et al., Computational and mathematical methods in medicine, 2013:546562; Zhang et al., IEEE reviews in biomedical engineering, 2014; 7:87-96]. The electromagnetic property can include, but is not limited to, at least one conductivity and/or permittivity.

Alternatively or additionally, the methods described herein can optionally include, using the absolute phase map of $B_1^+$, designing or evaluating the at least the portion of the transmit coil of the MRI system [Padormo et al., NMR in Biomedicine 2016; 29:1145-1161].

Alternatively or additionally, the methods described herein can optionally include, using the absolute phase map of $B_1^+$, performing quality control of the at least the portion of the transmit coil of the MRI system [Padormo et al., NMR in Biomedicine 2016; 29:1145-1161].

Alternatively or additionally, the methods described herein can optionally include, using the absolute phase map of $B_1^+$ or $B_1^-$, correcting MR signal inhomogeneity caused by both transmit and receiver coils of the MRI system [Wang et al., Magn Reson Med., 2005; 53(2):408-17; Wang et al., Magn Reson Med., 2005; 53(3):666-74].

Alternatively or additionally, the methods described herein can optionally include, using the an absolute phase map of either $B_1^+$ or $B_1^-$, determining at least one of a conductivity of a sample, a permeability of the sample, or an electromagnetic field distribution inside the sample [Zhang et al., IEEE reviews in biomedical engineering, 2014; 7:87-96]. For example, determining at least one of the conductivity or the permeability of the sample provides a biomarker for functional MRI, a diagnosis of disease, electromagnetic therapy, or human safety in electromagnetic environment. Additionally, the methods described herein can include determining local specific absorption rate (SAR) which is a measure of the rate at which energy is absorbed by the human body when exposed to a radio frequency (RF) electromagnetic field [Katscher et al., Magn Reson Med., 2012; 68:1911-1918; Katscher et al., IEEE transactions on medical imaging, 2009; 28:1365-1374].

Alternatively or additionally, the methods described herein can optionally include, using the absolute phase map of $B_1^+$ and $B_1^-$, improving the accuracy and precision of quantitative MRI [Li et al., Neuroimage, 2011; 55:1645-1656; Wang et al., J Magn Reson. 2006; 182(2):283-92] and MRS [Rodgers C T and Robson M D, Magn Reson Med. 2016; 75(2):473-87; Abdoli A and Maudsley A A, Magn Reson Med.2016; 76(3):733-41].

Alternatively or additionally, the methods described herein can optionally include, using the absolute phase map of $B_{1,t}^+$ and $B_{1,r}^-$, improving the accuracy and precision of phase contrast image [Peng et al., Magn Reson Med 2010; 64:472-480; Frahm J,et al. U.S. Pat. No. 9,529,066].

Data from array coil elements are optimally combined by the respective coils' complex sensitivity. Alternatively or additionally, the methods described herein can optionally include, using the absolute phase map of $B_1^-$, improving the image quality of the combined image and spectroscopy from multiple receivers [Kim et al., Magn Reson Med, 2016 in publication; Dagher J and Nael K., Magn Reson Med 2016; 75:1218-1231; Rodgers C T and Robson M D., Magn Reson Med 201675:473-487].

Alternatively or additionally, the methods described herein can optionally include, using the absolute phase map of $B_1^+$ and $B_1^-$, improving the image quality of image reconstruction from parallel acquisition [Kim et al., Magn Reson Med 2016 in publication; Dagher J and Nael K, Magn Reson Med, 2016; 75:1218-1231] and simultaneous multi-slice acquisition [Zhu et al., IEEE transactions on medical imaging, 2016; 35(8):1824-36].

Alternatively or additionally, the method can optionally include improving image quality and increasing accelerator factors for at least one of multiple transmit coil, multiband excitation, or multiple receive coil imaging techniques using the absolute phase $B_1^+$ map of transmit coil and/or the absolute phase of $B_1^-$ field of the receive coil. It should be understood that various MRI methods depend on the accuracy of the absolute phase $B_1^+$ map of transmit coil and/or the absolute phase of $B_1^-$ field of the receive coil. The absolute phase $B_1^+$ map of transmit coil and/or the absolute phase of $B_1^-$ field of the receive coil estimated according to the techniques described herein can therefore be used with other MRI methods, which can result in improvements due to the accuracy of the estimated absolute phase $B_1^+$ map of transmit coil and/or the absolute phase of $B_1^-$ field of the receive coil. For example, Pruessmann K P et al. disclosed a method called SENSE: sensitivity encoding for fast MRI in Magn Reson Med 1999; 42:952-962 using the complex information of $B_1^-$ field of the receive coil. The SENSE method strongly depends on the accuracy of the complex $B_1^-$ field. Additionally, Cauley S F et al. disclosed the method in Magn Reson Med. 2017; 78:1093-1099 to improve the parallel imaging reconstruction using autocalibrated wave-CAIPI reconstruction. The Wave-CAIPI reconstruction and their variations modified the phase encoding sampling strategy to shift the spatial aliasing pattern to reduce aliasing and better exploit the coil sensitivity variation. The techniques described herein for estimating absolute phase $B_1^+$ map of transmit coil and/or the absolute phase of $B_1^-$ field of the receive coil therefore provide the ability to characterize the coil sensitivity variation accurately. This will help the further improvement of Wave-CAIPI reconstruction and their variations in image quality and accelerator factors. Additionally, Gagoski B A, et al. in Magn Reson Med. 2015; 73:929-938 disclosed a method to improve image quality and accelerator factors for simultaneous multislice (SMS) imaging using Wave-CAIPI acquisition with reduced g-factor penalty. Similarly, accurate absolute phase map of $B_1^+$ of transmit coil, which can be estimated according to the techniques described herein, can improve image quality and accelerator factors.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for determining spatial distribution of an absolute phase of radio frequency (RF) transmit field $B_1^+$ in a magnetic resonance imaging (MRI) system, comprising:

selecting a transmit coil for which to measure the absolute phase of the RF transmit field $B_1^+$;

exciting nuclear spins in magnetic resonance (MR) nuclei using at least two transmit configurations of the transmit coil;

detecting first MR signals and second MR signals arising from exciting nuclear spins in MR nuclei using a first transmit configuration and a second transmit configuration, respectively;

acquiring a first set of complex k-space data and a second set of complex k-space data from the first MR signals and the second MR signals, respectively; and estimating an absolute phase $B_1^+$ map of the transmit coil using the first set of complex k-space data and the second set of complex k-space data.

2. The method of claim 1, further comprising transforming the first set of complex k-space data and the second set of complex k-space data into a first image and a second image, respectively, wherein estimating an absolute phase $B_1^+$ map of the transmit coil further comprises using the first image and the second image.

3. The method of claim 1, further comprising estimating an absolute phase of $B_1^+$ transmit field for an arbitrary transmit coil using the absolute phase $B_1^+$ map of the transmit coil as a reference.

4. The method of claim 1, further comprising applying the absolute phase $B_1^+$ map of the transmit coil to improve image quality of simultaneous multi-slice excitation.

5. The method of claim 1, further comprising applying the absolute phase $B_1^+$ map of the transmit coil to improve performance of RF shimming and/or parallel transmit field.

6. The method of claim 1, further comprising applying the absolute phase $B_1^+$ map of the transmit coil to estimate changes of electromagnetic field caused by an electromagnetic property of an object being imaged.

7. A method for determining spatial distribution of an absolute phase of radio frequency (RF) receive field $B_1^-$ in a magnetic resonance imaging (MRI) system, comprising:

exciting nuclear spins in magnetic resonance (MR) nuclei using a transmit coil of the MRI system;

detecting MR signals arising from exciting nuclear spins in MR nuclei using a receive coil of the MRI system;

acquiring a complex image from the MR signals;

estimating a phase of the complex image;

receiving an absolute phase $B_1^+$ map of the transmit coil of the MRI system; and estimating an absolute phase of $B_1^-$ field of the receive coil using the absolute phase $B_1^+$ map of the transmit coil of the MRI system and the phase of the complex image.

8. The method of claim 7, further comprising receiving an inhomogeneous $B_0$ map, wherein the absolute phase of $B_1^-$ field of the receive coil is estimated using the absolute phase $B_1^+$ map of the transmit coil of the MRI system, the phase of the complex image, and the inhomogeneous $B_0$ map.

9. The method of claim 7, wherein the complex image is the same complex image used for estimating the absolute phase of the $B_1^+$ map of the transmit coil of the MRI system.

10. The method of claim 7, wherein the complex image is a different complex image than that used for estimating the absolute phase of the $B_1^+$ map of the transmit coil of the MRI system.

11. The method of claim 7, further comprising applying the absolute phase of $B_1^-$ field of the receive coil to improve image quality of both magnitude image and phase image from parallel image reconstruction.

12. The method of claim 7, further comprising applying the absolute phase of $B_1^-$ field of the receive coil to estimate changes of electromagnetic field caused by an electromagnetic property of an object being imaged.

13. The method of claim 7, further comprising applying the absolute phase of $B_1^-$ field of the receive coil to improve the quality of both image and spectroscopy signal combination from each receive channel.

14. The method of claim 7, further comprising applying the absolute phase of $B_1^-$ field of the receive coil to improve the qualitative image and qualitative spectroscopy.

15. The method of claim 7, further comprising combining with various fast imaging techniques at least one of parallel imaging acquisition, under-sampling acquisition, compensate sense, or simultaneous multiple-slice excitation, to reduce a scanning time for estimating the absolute phase of $B_1^-$ field of the receive coil.

16. The method of claim 7, wherein the estimation of the absolute phase of $B_1^-$ field of the receive coil provides information associating an estimated electrical property with a pathological state of tissues in a subject.

17. The method of claim 7, further comprising combining with various image sequences and techniques at least one of gradient echo-based sequences, spin-echo-based sequences, echo planar imaging (EPI) based sequences, or ultra-short echo time sequences, to reduce or remove the effect of $B_0$ inhomogeneity on the absolute phase of $B_1^-$ field of the receive coil.

18. The method of claim 7, further comprising determining specific energy absorption rate (SAR) using the absolute phase of $B_1^-$ field of the receive coil.

19. The method of claim 7, wherein the absolute phase of $B_1^-$ field of the receive coil is used to improve image quality and increase accelerator factors for at least one of multiple transmit coil, multiband excitation, or multiple receive coil imaging techniques.

20. A magnetic resonance imaging (MRI) system for determining spatial distribution of an absolute phase of radio frequency (RF) transmit field $B_1^-$ of a receive coil, comprising:

a transmitting and receiving unit comprising at least one RF coil, wherein the transmitting and receiving unit is configured to:

excite nuclear spins in magnetic resonance (MR) nuclei using a transmit coil of the MRI system, and detect MR signals using a receive coil of the MRI system; and an MRI system controller operably coupled with the transmitting and receiving unit, the MRI system controller comprising a processor and a memory, the memory having computer-executable instructions stored thereon that, when executed by the processor, cause the processor to:

acquire a complex image from the MR signals;

estimate a phase of the complex image;

receive an absolute phase $B_1^+$ map of the transmit coil of the MRI system; and estimate an absolute phase of $B_1^-$ field of the receive coil using the absolute phase $B_1^+$ map of the transmit coil and the phase of the complex image.

21. The system of claim 20, the memory having computer-executable instructions stored thereon that, when executed by the processor, cause the processor to receive an inhomogeneous $B_0$ map, and wherein the absolute phase of $B_1^-$ field of the receive coil is estimated using the absolute phase $B_1^+$ map of the transmit coil of the MRI system, the phase of the complex image, and the inhomogeneous $B_0$ map.

22. The system of claim 20, wherein the complex image is the same complex image used for estimating the absolute phase $B_1^+$ map of the transmit coil of the MRI system.

23. The system of claim 20, wherein the complex image is a different complex image than that used for estimating the absolute phase of the $B_1^+$ map of the transmit coil of the MRI system.

* * * * *